(12) United States Patent
Valkirs

(10) Patent No.: US 6,503,722 B1
(45) Date of Patent: *Jan. 7, 2003

(54) DIAGNOSTIC TESTS AND KITS FOR CLOSTRIDIUM DIFFICILE

(75) Inventor: Gunars E. Valkirs, Escondido, CA (US)

(73) Assignee: Biosite Diagnostics, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/363,960

(22) Filed: Jul. 29, 1999

Related U.S. Application Data

(62) Division of application No. 08/832,935, filed on Apr. 4, 1997, now Pat. No. 5,965,375.

(51) Int. Cl.⁷ ...................... G01N 33/53; G01N 33/554; G01N 33/543; G01N 33/544
(52) U.S. Cl. .......................... 435/7.2; 435/7.32; 435/7.9; 435/7.92; 435/7.94; 435/7.95; 435/26; 435/973; 436/518; 436/528; 436/531; 436/532; 436/808; 436/811
(58) Field of Search ................................. 435/7.2, 7.32, 435/7.9, 7.92, 7.94, 7.95, 26, 973, 975; 436/518, 528, 531, 532, 808, 811; G01N 33/53, 33/554, 33/543, 33/544

(56) References Cited

U.S. PATENT DOCUMENTS

| | | |
|---|---|---|
| 4,533,630 A | 8/1985 | Wilkins et al. |
| 4,554,088 A | 11/1985 | Whitehead et al. |
| 4,628,037 A | 12/1986 | Chagnon et al. |
| 4,672,040 A | 6/1987 | Josephson |
| 4,695,392 A | 9/1987 | Whitehead et al. |
| 4,695,393 A | 9/1987 | Whitehead et al. |
| 4,879,218 A | 11/1989 | Wilkins et al. |
| 5,071,759 A | 12/1991 | Rothman et al. |
| 5,965,375 A | * 10/1999 | Valkirs ........................ 435/7.2 |

FOREIGN PATENT DOCUMENTS

WO WO 92/18866 10/1992

OTHER PUBLICATIONS

Sweet, M.D., et al., "Triage C. difficile panel, a rapid immunoassay device for the simultaneous detection of C. difficile toxin A and glutamate dehydrogenase in stool," Biological Abstracts/RRM, Jul. 22, 1997 the abstract No. 119706.

J.L. Staneck, et al., "Multicenter Evaluation of Four Methods for Clostridium difficile Detection: ImmunoCard C. difficile, Cytotoxin Assay, Culture, and Latex Agglutination," Journal of Clinical Microboilogy, Nov. 1996, pp. 2718–2721.

D. Gerding, et al., "Optimal Methods for identifying Clostridium difficile Infections," Clinical Infectious Diseases, 1993, vol. 16, pp. S439–S442.

J.S. Brazier, "Role of the Laboratory in Investigations of Clostridium difficile Diarrhea," Clinical Infectious Diseases, 1993, vol. 16, pp S228–S233.

A.C. Fluit, et al., "Nontoxigenic Strains of Clostridium difficile Lack the Genes for Both Toxin A and Toxin B," Journal of Clinical Microbiology, Nov. 1991, pp. 2666–2667.

M.J. Wofhagen, et al., "Rapid Detection of Toxigenic Clostridium difficile in Fecal Samples by Magnetic Immuno PCR Assay," Journal of Clinical Microbiology, Jul. 1994, pp. 1629–1633.

F. Barbut, et al., "Comparison of Three Enzyme Immunoassays, a Cytotoxicity Assay, and Toxigenic Culture for Diagnosis of Clostridium difficile–Associated Diarrhea," Journal of Clinical Microbiology, Apr. 1993, pp. 963–967.

C.C. Knapp, "Comparison of Vidas Clostridium difficile toxin–A Assay and Premier C. difficile Toxin–A Assay to Cytotoxin–B tissue Culture Assay for the Detection of Toxins of C. difficile," Diagnostic Microbiology and Infectious Diseases, 1993, vol. 17, pp. 7–12.

Y.J. Tang, "Specific detection of Clostridium difficile toxin–A gene sequences in clinical isolates," Molecular and Cellular Probes, 1994, vol. 8, pp. 463–467.

D.E. McMillin, et al., "Simultaneous detection of toxin A and toxin B genetic determinants of Clostridium difficile using the multiplex ploymerase chain reaction," Can. J. Microbiology, Chemical Abstracts, vol. 117, No. 7, Aug. 17, 1992, p. 203, col. 1, the abstract No. 63878x.

D.P. Forhan, et al., "A Rapid Assay for the Detection of Clostridium difficile Toxin A and Toxin B Using Latex–Based Agglutination Technology," Clinical Chemistry, Jun. 1996, vol. 42, p. S109, abstract No. 058.

J.K. Teller, et al., "The glutamate degydrogenase gene of Clostridium symbiosum: Cloning by polyerase chain reaction, sequence analysis, and over–expression in Escherichia coli," European Journal of Biochemistry, 1992, vol. 206, pp. 151–159.

D.M. Lyerly et al., Journal of Clinical Microbiology (Nov. 1991) 29(11): 2639–2642.

L.R. Peterson, et al., Infectious Disease Clinics of North America (Jun. 1993) 7(2): 277–293.

D.M. Lyerly et al., Infection and Immunity (Oct. 1986) 54(1): 70–76.

L.R. Peterson et al., Laboratory Management (Apr. 1988) 26(4): 42–45.

D.M. Lyerly et al., Clinical Microbiology Reviews (Jan. 1988) 1(1): 1–18.

* cited by examiner

Primary Examiner—Lynette R. F. Smith
Assistant Examiner—Padma Baskar
(74) Attorney, Agent, or Firm—Townsend and Townsend and Crew LLP

(57) ABSTRACT

This invention provides methods, compositions, and kits for detecting the presence of toxigenic strains of C. difficile in a biological sample. One embodiment provides methods for C. difficile detection that involve assaying for both C. difficile glutamate dehydrogenase and C. difficile toxin A or toxin B. In another embodiment, the invention provides a highly sensitive assay for C. difficile toxin A that is useful for determining whether a C. difficile strain is toxigenic. This embodiment involves binding of toxin A to a moiety that reversibly binds to a capture moiety present on a magnetic bead. A magnetic field is applied to the sample to concentrate the toxin A, after which the magnetic beads are dissociated and removed from the solution to obtain a highly concentrated preparation of toxin A, thus making possible a very sensitive assay.

10 Claims, 4 Drawing Sheets

Figure 1

FLAG PEPTIDE MARKER

Enterokinase Cleavage

Eight Amino Acid FLAG MAb Binding Site

N - Asp - Tyr Lys Asp Asp Asp Asp Lys

5' - GAC TAC AAG GAC GAC GAT GAC AAG - 3'

3' - CTG ATG TTC CTG CTG CTA CTG TTC - 5'

Schematic Diagram of Highly Sensitive Assay for *C. difficile* Toxin A

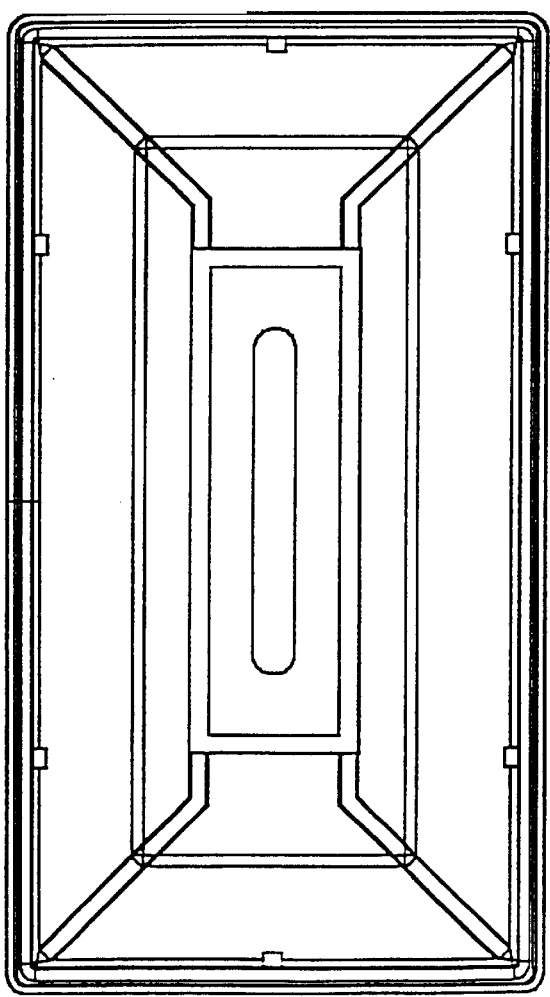
Figure 4A
Figure 4B
Figure 4C

DIAGNOSTIC TESTS AND KITS FOR *CLOSTRIDIUM DIFFICILE*

This application is a division of and claims priority from U.S. patent application Ser. No. 08/832,935 (now U.S. Pat. No. 5,965,375), filed Apr. 4, 1997. This application is related to co-filed U.S. applications U.S. Ser. Nos. 60/044,292 (abandoned), 08/835,159 (pending) and 08/832,985 (pending). These applications are incorporated by reference in their entirety for all purposes.

BACKGROUND OF THE INVENTION

1. Field of the Invention

This invention pertains to the field of diagnostic methods and kits for detecting *Clostridium difficile*. The methods and kits provide rapid, sensitive, and accurate assays for the presence of toxigenic strains of *C. difficile* in an biological sample.

2. Background

*Clostridium difficile*, an anaerobic organism, is the major causative agent of pseudomembranous colitis (PMC) in humans. PMC is characterized by diarrhea, a severe inflammation of the colonic mucosa, and formation of pseudomembranes that are composed of fibrin, mucus, necrotic epithelial cells, and leukocytes. The pseudomembrane can form a sheath over the entire colonic mucosa. In addition to causing PMC, *C. difficile* is believed to play a role in other less severe gastrointestinal illnesses; the organism is estimated to cause approximately 25% of reported cases of antibiotic-associated diarrhea. Brettle and Wallace (1984) *J. Infect.* 8: 123–128; Gilligan et al. (1981) *J. Clin. Microbiol.* 14: 26–31. Diarrhea affects approximately 25 million persons annually in the US alone, and causes almost 11,000 deaths. Peterson and Kelly (1993) *Lab. Diagnosis Infect. Dis.* 7: 277–292. *C. difficile*-caused diseases are not limited to gastrointestinal illnesses, as the organism can cause abscesses, wound infections, osteomyelitis, urogenital tract infections, septicemia, peritonitis, and pleuritis. Lyerly et al. (1988) *Clin. Microbiol. Rev.* 1: 1–18; Hafiz et al. (1975) *Lancet* 1: 420–421; Levett (1986) *J. Infect.* 12: 253–263; Saginur et al. (1983) *J. Infect. Dis.* 147: 1105. Antibiotics can predispose a host animal to PMC and other *C. difficile*-related illnesses, as the disturbance of the normal bacterial flora by the antibiotic disrupts the major barrier against colonization by pathogens, rendering the host animal susceptible to colonization by pathogens such as *C. difficile*. Hospitals and chronic care facilities are significant sources of *C difficile* infection, with one study finding that 21% of patients acquired *C. difficile* infection during hospitalization. McFarland et al. (1989) *N. Engl. J. Med.* 320: 204.

The high frequency of *C. difficile* infection, coupled with the likelihood of a poor clinical outcome for cases that are not treated promptly, makes clear the need for rapid and accurate tests to detect *C. difficile* infection, determine whether any *C. difficile* present is toxigenic, and evaluate the effectiveness of treatment. Previously available methods for detecting *C. difficile* are much less than optimal for effective diagnosis and treatment of infection. One previously known method for detecting *C. difficile* infection is culture on agar media. The efficacy of this method is hampered by the significant variation in results that are obtained using different media, and the high rate of false positives (10–29%). Peterson and Kelly, supra. An additional disadvantage of this method is the lengthy culture period required before visible *C. difficile* colonies are discernable. A commercially available assay for *C. difficile* involves latex agglutination of an antigen that was eventually identified as *C. difficile* glutamate dehydrogenase. Lyerly et al. (1991) *J. Clin. Microbiol.* 29: 2639; Lyerly et al. (1986) *J. Clin. Microbiol.* 23: 622. However, this assay suffers from widely varying and insufficient sensitivity and specificity, with sensitivity ranging from 68% to 93% and specificity between 80% and 95%. Peterson and Kelly, supra. Moreover, previously available glutamate dehydrogenase assays were not thought to be useful for detection of toxigenic strains of *C. difficile* because glutamate dehydrogenase is produced by non-toxigenic strains of *C. difficile*, as well as toxigenic strains.

Non-toxigenic strains of *C. difficile* are generally considered clinically insignificant, while toxigenic strains can be lethal. Although distinguishing between toxigenic and non-toxigenic *C. difficile* strains is thus of great importance, previously known assays that were used in attempts to accomplish this goal were ineffective. One commonly used diagnostic method for detecting the presence of toxigenic *C. difficile* involves determining whether *C. difficile* is cytotoxic to susceptible cell lines. This cytotoxicity is the result of either or both of the two toxins produced by *C. difficile*, an enterotoxin designated toxin A and a cytotoxin designated toxin B, both of which are believed to be involved in the pathogenesis of PMC. The cytotoxicity assay has significant drawbacks for clinical use however, including the need to maintain tissue culture lines and the relatively low sensitivity of the assay. For example, Peterson and Kelly, supra., found that the sensitivity of cytotoxin detection alone ranged from 67% to 100%, and other researchers found sensitivity to be as low as 71%. Demlee et al. (1985) *J. Clin. Microbiol.* 21: 323. Immunoassays for toxins A and/or B have also been used to detect *C. difficile* in samples, but these methods suffer from low sensitivity (63% to 88%). Peterson and Kelly, supra.

Thus, a need exists for assays to detect the presence of *C. difficile* in a sample that are rapid, sensitive, specific, and cost-effective. Assays to determine whether an infecting *C. difficile* strain is toxigenic are also needed. The present invention fulfills these and other needs.

SUMMARY OF THE INVENTION

The present invention provides methods, compositions, and kits for the rapid detection of *C. difficile* in a test sample, in particular for detection of toxigenic *C. difficile* strains.

In a first embodiment, the methods involve detecting *C. difficile* toxin A or toxin B, and also detecting *C. difficile* glutamate dehydrogenase. The assay means for detecting the *C. difficile* antigens can be, for example, immunoassays. Sandwich assays provide a convenient, sensitive method for performing the methods. In one embodiment, the assay involves detection of *C. difficile* toxin A using a sandwich assay that employs an anchor moiety that is immobilized on a solid support and specifically binds to at least a first epitope of *C. difficile* toxin A, and one or more detection moieties, each of which is conjugated to a detectable label and specifically binds to at least a second epitope of *C. difficile* toxin A. The assay for detecting *C. difficile* glutamate dehydrogenase can also involve a sandwich assay in which glutamate dehydrogenase is bound to an immobilized anchor moiety that specifically binds to at least a first epitope of *C. difficile* glutamate dehydrogenase, after which bound glutamate dehydrogenase is detected using one or more detection moieties, each of which is conjugated to a detectable label and specifically binds to at least a second epitope of *C. difficile* glutamate dehydrogenase. The anchor moiety that specifically binds *C. difficile* toxin A and the anchor moiety that specifically binds *C. difficile* glutamate dehydrogenase can be immobilized in separate zones on a single solid support, on separate supports, or can both be present in a single zone.

The invention also provides devices for detecting the presence of toxigenic strains of *C. difficile* in a test sample. The devices include a porous member having an upper and a lower surface, being positioned in the device such that the test sample may be applied to the upper surface, wherein a plurality of anchor moieties that are capable of specifically binding to *C. difficile* toxin A are immobilized in a first zone of the porous member, and a plurality of anchor moieties that are capable of specifically binding to *C. difficile* glutamate dehydrogenase are immobilized in a second zone of the porous member. The devices also include a non-absorbent member having a textured surface with channels capable of forming a network of capillary channels when placed in communication beneath or around the porous member, said-capillary network being substantially parallel to the lower surface of the porous member. The test sample, alone or in combination with other fluids, when applied to the upper surface is drawn through the porous member to the capillary network formed between the porous member and the non-absorbent member when substantially all the void volume of the porous member is filled with the test sample and when contact is made between the porous member and the non-absorbent member.

Kits for performing these assays for *C. difficile* are also provided by the present invention. The kits can include a container that includes some or all of the reagents and methods for carrying out the assays. For example, a kit can include a solid support upon which is immobilized an anchor moiety that specifically binds to *C. difficile* toxin A and an anchor moiety that specifically binds to *C. difficile* glutamate dehydrogenase. Also included in the kits can be a detection moiety that specifically binds to *C. difficile* toxin A, a detection moiety that specifically binds to *C. difficile* glutamate dehydrogenase, and reagents useful for detecting the presence of two different detectable labels present on each of the detection moieties. Written instructions as to how to use the kit to assay for the presence of *C. difficile* toxin A and glutamate dehydrogenase in a test sample can also be provided in the kits. The kits can also include, as controls, *C. difficile* toxin A and/or glutamate dehydrogenase; the *C. difficile* antigen can be complexed with the anchor moiety in a control zone of the solid support.

Another embodiment of the invention provides methods, compositions, and kits for detecting the presence of toxigenic *C. difficile* strains in a test sample by performing a highly sensitive assay for *C. difficile* glutamate dehydrogenase. These methods are capable of detecting the presence of toxigenic *C. difficile* in samples that would have tested negative for toxigenic *C. difficile* using previously available assays. One method of performing the highly sensitive assays is to contact the sample with a solid support to which is bound an anchor moiety that is specific for at least a first epitope of *C. difficile* glutamate dehydrogenase for a time sufficient for some or all of the glutamate dehydrogenase to bind to the anchor moiety. The bound *C. difficile* glutamate dehydrogenase is then contacted with one or more detection moieties, each of which includes a detectable label and a binding moiety that is capable of specifically binding to at least a second epitope of *C. difficile* glutamate dehydrogenase. The presence of bound detectable label is indicative of toxigenic *C. difficile* in the sample.

Another embodiment of the invention provides methods for accurately determining whether a test sample contains a toxigenic strain of *C. difficile* by testing for the presence of *C. difficile* glutamate dehydrogenase in the test sample, and, if *C. difficile* glutamate dehydrogenase is present in the test sample, testing for the presence of *C. difficile* toxin A or toxin B in the sample. Preferably, the toxin A or toxin B assay has a sensitivity of at least about 2 ng toxin per ml. Any of several assays can be used to detect the *C. difficile* antigens. For example, the testing for the presence of *C. difficile* toxin A or toxin B can involve amplification of a nucleic acid that encodes toxin A or toxin B, or a portion of said nucleic acid, by polymerase chain reaction and detecting the presence of the amplified nucleic acid. Toxin B can be detected by means of a cytotoxicity assay. Additional high sensitivity assays for use in these methods are described herein.

In another embodiment, the invention provides methods for concentrating *C. difficile* toxin A from a test sample by using magnetic particles. These methods involve adding to the test sample a toxin A binding moiety that specifically binds to *C. difficile* toxin A to form a binding moiety-toxin A complex, and adding to the test sample a magnetic bead to which is attached a capture moiety that specifically binds to the toxin A binding moiety to form a magnetic bead-binding moiety-toxin A complex. The magnetic bead-binding moiety-toxin A complex is separated from the test sample, after which the binding moiety-toxin A complex is dissociated from the magnetic bead. The magnetic bead can then be separated from the solution containing the binding moiety-toxin A complex and the presence of the binding moiety-toxin A complex is then detected. In a preferred embodiment of the magnetic bead-based toxin A concentration method, the binding of the capture moiety to the toxin A binding moiety is reversible under relatively mild conditions. Reversible binding can be achieved by linking to the toxin A binding moiety a molecular tag to which the capture moiety binds. The molecular tag and the corresponding capture moiety are chosen so as to dissociate under conditions that do not disrupt the ability of the toxin A binding moiety to bind to the toxin A. If the dissociation conditions also cause the toxin A binding moiety and toxin A to dissociate, then following separation of the magnetic beads, the concentrated toxin A solution can be modified so that the toxin A binding moiety and the toxin A can immediately reassociate. For example, if the pH of the solution was increased in order to effect dissociation of the magnetic beads from the toxin A binding moiety, after separation of the beads the solution can be modified by neutralization.

Another embodiment of the invention provides methods of detecting toxin A that has been concentrated using the methods described herein. The detection method can involve applying the solution containing a toxin A binding moiety-toxin A complex prepared as above to a solid support upon which is immobilized an anchor moiety that is capable of specifically binding to an epitope of *C. difficile* toxin A that is different than the toxin A epitope to which the toxin A binding moiety binds. A detection moiety that is capable of specifically binding to the toxin A binding moiety, or to a hapten attached to the binding moiety, is used to detect the presence of immobilized toxin A and associated toxin A binding moiety.

Kits provided by the invention can include a toxin A binding moiety that specifically binds to *C. difficile* toxin A, a magnetic bead to which is attached a capture binding moiety that specifically binds to the toxin A binding moiety, a solid support upon which is immobilized an anchor binding moiety that specifically binds to at least one epitope of *C. difficile* toxin A that is different than the toxin A epitope to which the toxin A binding moiety binds, and a detection moiety that is conjugated to a detectable label and specifically binds to a hapten present on the toxin A binding moiety.

BRIEF DESCRIPTION OF THE DRAWINGS

FIG. 1 shows the amino acid sequence (SEQ ID NO. 1) of a FLAG peptide marker, and a nucleotide sequence (SEQ ID NO. 2) that codes for this peptide. Also shown is a cleavage site for an enterokinase.

FIG. 3A is a top view, showing an elongated well in the center. FIG. 3B is a section view of the top piece, showing a membrane that is ultrasonically welded to the underside of the top piece. FIG. 3C is an end view of the top piece of the apparatus.

FIGS. 4A–4C show a bottom piece of an apparatus for performing an immunoassay for simultaneous detection of *C. difficile* glutamate dehydrogenase and toxin A. FIG. 4A is a top view, FIG. 4B is a section view, and FIG. 4C is an end view of the bottom piece. To construct a complete apparatus, a bottom piece is joined to a top piece such as is shown FIGS. 3A–3C.

DETAILED DESCRIPTION

Figure 2:
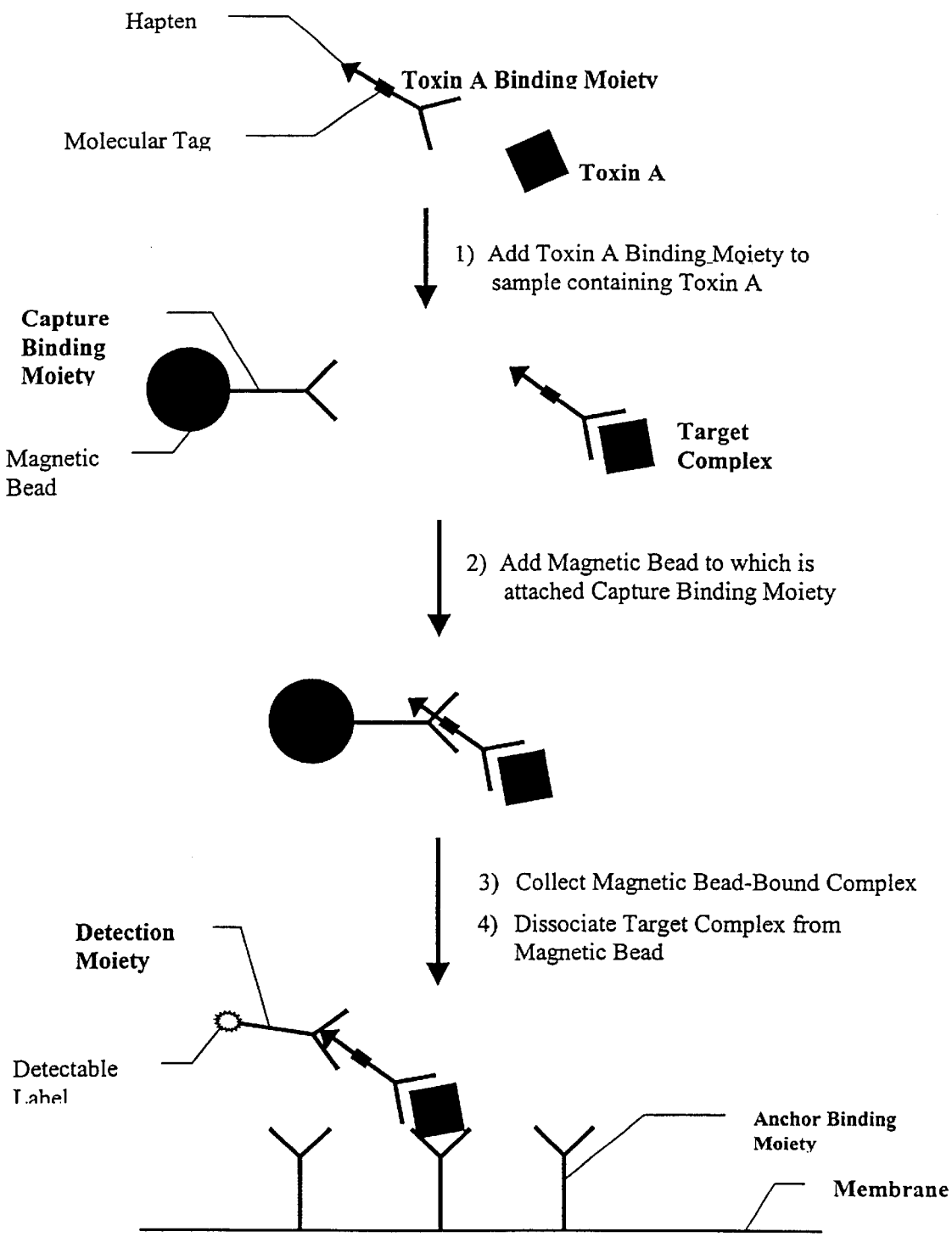
FIG. 2 shows a schematic diagram of a high sensitivity assay that is useful for detecting *C. difficile* toxin A.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display. See, e.g., Paul, *Fundamental Immunology*, $3^{rd}$ Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988) *Antibodies, A Laboratory Manual,* Cold Spring Harbor Publications, New York, for a description of immunoassay formats and conditions that can be used to determine specific immunoreactivity. Typically a specific or selective reaction will be at least twice background signal to noise and more typically more than 10 to 100 times background.

DESCRIPTION OF THE PREFERRED EMBODIMENTS

The present invention provides methods, kits and compositions for detecting *Clostridium difficile* in a test sample.

The assays provide a rapid, accurate and cost-effective assay for *C. difficile* infection. Unlike other *C. difficile* assay methods, the methods of the invention are both sensitive and specific, and are able to accurately determine whether or not an infecting *C. difficile* strain is toxigenic. In one embodiment, the invention provides methods, compositions and kits for performing an assay for *C. difficile* infection by determining the presence or absence of two different *C. difficile* antigens, glutamate dehydrogenase and toxin A. A second embodiment of the invention provides methods, compositions, and kits that are useful for determining with a high degree of accuracy whether a test sample contains a *C. difficile* strain that is toxigenic. This embodiment also provides a highly sensitive assay for *C. difficile* toxin A that is capable of detecting toxin A at levels that are undetectable by other methods that are readily adaptable for use in the clinic. Also provided are highly sensitive assays for toxigenic strains of *C. difficile* that involve detecting the presence of *C. difficile* glutamate dehydrogenase.

The methods, compositions and kits provided by the instant invention are useful for detecting *C. difficile* infection in test samples, including biological samples such as cultures, tissue samples bodily fluids, and the like. Typically, the biological sample analyzed for *C. difficile* infection will be a stool sample. For liquid or semi-solid stool samples, a portion of the sample is added to an assay container and, optionally, diluted with a suitable diluent such as water or an appropriate buffer and mixed. Suitable buffers include, for example, buffered protein solutions and the like. Solid stool samples can be placed in a diluent and suspended by vigorous mixing. Typically, the sample is diluted sufficiently to provide a solution of suitable clarity for use in the assays; this is generally about a 3–20 fold dilution, with about a 10-fold dilution being typical. After mixing, one can clarify the sample by, for example, filtration or centrifugation or other methods known to those of skill in the art. In general, well known methods for preparing test samples for assays, such as immunoassays, are suitable for preparing test samples for analysis using the methods provided by the claimed invention. Both toxin A and glutamate dehydrogenase are generally found in soluble form, both in culture and in biological samples. However, the claimed methods are also useful for detecting these antigens on the surface of *C. difficile* cells, as well as soluble antigens.

I. Rapid Detection of *C. Difficile* Infection by Combined Glutamate Dehydrogenase and Toxin A Assay In a first embodiment, the present invention provides methods, compositions, and kits for rapid detection of toxigenic strains of *C. difficile* in a test sample. These methods involve an assay means for detecting *C. difficile* glutamate dehydrogenase and an assay means for detecting *C. difficile* toxin A. By detecting both glutamate dehydrogenase and toxin A, the methods provides greater sensitivity and specificity in detecting toxigenic *C. difficile* strains than assaying for either *C. difficile* antigen alone. Toxigenic *C. difficile* strains, which are of particular clinical interest because it is these strains that are the causative agents of diseases such as pseudomembranous colitis in humans, produce toxin A. Non-toxigenic strains, which are not believed to have adverse effects on humans or other animals, do not produce toxin A. Glutamate dehydrogenase is produced by *C. difficile* at much higher levels than is toxin A, so the inclusion of a glutamate dehydrogenase assay in the claimed invention provides a high degree of sensitivity.

The assay means for detecting *C. difficile* glutamate dehydrogenase and *C. difficile* toxin A are, in one embodiment, binding assays. In these assays, which include immunoassays, glutamate dehydrogenase and toxin A are detected using detection moieties that are capable of specifically binding to the respective *C. difficile* antigen. The detection moieties include at least a binding component and a detectable label. Suitable binding components include any moiety that is capable of specifically binding to *C. difficile* glutamate dehydrogenase or to toxin A. Antibodies and fragments thereof are examples of binding components that are suitable for use in detection moieties.

Various procedures known in the art can be used for the production of antibodies that specifically bind to *C. difficile* glutamate dehydrogenase or toxin A. For the production of polyclonal antibodies, one can use the respective *C. difficile* antigen to inoculate any of various host animals, including but not limited to rabbits, mice, rats, sheep, goats, and the like. Glutamate dehydrogenase, for example, can be prepared by recombinant means using an expression vector containing a gene encoding the enzyme; the complete nucleotide sequence is available in GenBank, Accession No. M65250. Polyclonal and monoclonal antibodies can also be prepared using recombinant techniques. Monoclonal antibodies can be prepared by any technique that provides for the production of antibody molecules by-continuous cell lines in culture, including the hybridoma technique originally developed by Kohler and Milstein ((1975) *Nature* 256: 495–497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77–96). Monoclonal antibodies also can be produced in germ-free animals as was described in PCT/US89/02545 (Publication No. WO/8912690, published Dec. 12, 1989). One example of a suitable antibody for use in a detection moiety for *C. difficile* toxin A is the recombinantly produced polyclonal antibody CD.TXA.1.PC. An example of a suitable antibody for use in a detection moiety for *C. difficile* glutamate dehydrogenase is CD.43.9, which is a recombinantly produced monoclonal antibody. Each of these antibodies was prepared as described in co-filed, commonly assigned U.S. patent applications Ser. Nos. 08/835,159 and 08/832,985 (filed Apr. 4, 1997. Cells that produce each of these antibodies have been deposited under the Budapest Treaty with the American Type Culture Collection (12301 Parklawn Drive, Rockville Md. 20852) on Apr. 3, 1997, and have been assigned ATCC Accession Nos. 98388 (CD.TXA.1.PC) and 98390 (CD.43.9).

Fragments of antibodies are also useful as binding moieties. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies are also useful to construct detection moieties. Methods for producing single chain antibodies were described in, for example, U.S. Pat. No. 4,946,778. Techniques for the construction of Fab expression libraries were described by Huse et al. (1989) *Science* 246: 1275–1281; these techniques facilitate rapid identification of monoclonal Fab fragments with the desired specificity for toxin A or glutamate dehydrogenase. Suitable binding moieties also include those that are obtained using methods such as phage display.

The detection moieties used in the claimed invention will generally include, in addition to the binding moiety, a detectable label. Suitable detectable labels include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents that described the use of such labels include U.S. Pat. Nos. 3,817,837; 3,850,752; 3,939,350; 3,996,345; 4,277,437; 4,275,149; and 4,366,241. See also *Handbook of Fluorescent Probes and Research Chemicals* (6$^{th}$ Ed., Molecular Probes, Inc., Eugene Oreg.). Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. For use of the present invention in the clinic, preferred labels are non-radioactive and readily detected without the necessity of sophisticated instrumentation. Preferably, detection of the labels will yield a visible signal that is immediately discernable upon visual inspection.

A preferred format for use of the claimed methods in the clinical setting involves detecting *C. difficile* glutamate dehydrogenase and toxin A after these analytes are immobilized on a solid support. Suitable supports include, for example, nitrocellulose membranes, nylon membranes, and derivatized nylon membranes, and also particles, such as agarose, a dextran-based gel filtration medium such as SEPHADEX™ (Amersham Pharmacia Biotech, Piscataway N.J., and the like. To immobilize the *C. difficile* antigens on the solid support, two types of anchor moiety are non-diffusively associated with the support. One anchor moiety type is capable of specifically binding to *C. difficile* glutamate dehydrogenase and the other capable of specifically binding to *C. difficile* toxin A. Anchor moieties can be any compound that specifically binds to the respective *C. difficile* antigen. Antibodies that are specific for the respective *C. difficile* antigen, and fragments of such antibodies, are examples of anchor moieties that are suitable for use in the assays of the invention. A suitable anchor moiety that specifically binds to *C. difficile* glutamate dehydrogenase is the recombinant polyclonal antibody CD.43.5.PC, which was prepared as described in copending, commonly assigned U.S. patent application Ser. No. 08/832,985 (filed on Apr. 4, 1997.Cells that produce these antibodies were deposited under the Budapest Treaty with the American Type Culture Collection (12301 Parklawn Drive, Rockville Md. 20852) on Apr. 3, 1997, and have been assigned ATCC Accession No. 98389. A suitable anchor moiety for *C. difficile* toxin A is PCG-4, which is described in U.S. Pat. No. 4,533,630.

The anchor moieties can be non-diffusively immobilized on the support either by covalent or non-covalent methods, which are known to those of skill in the art. See, e.g., Pluskal et al. (1986) *BioTechniques* 4: 272–283. Conveniently, the anchor moiety for glutamate dehydrogenase and the anchor moiety for toxin A are immobilized on adjacent solid supports, or more preferably in different zones of the same solid support. Each discrete anchor moiety zone can be used to complete a different immunochemical reaction, thus permitting one to perform immunochemical reactions for both *C. difficile* antigens simultaneously. In another embodiment, where the detection moieties for the two *C. difficile* antigens each use a different label that is detectable in the presence of a signal from the label on the detection moiety for the second antigen, the anchor moieties for both antigens can be immobilized in the same zone of a single solid support.

The assays can be performed in any of several formats. For example, a sandwich assay can be performed by preparing a biological sample as discussed above, or as is otherwise appropriate for the particular sample, and placing the sample in contact with a solid support to which is immobilized a plurality of anchor moieties for *C. difficile* glutamate dehydrogenase and a plurality of anchor moieties for *C. difficile* toxin A. The *C. difficile* toxin A and glutamate dehydrogenase antigens, if present in the sample, bind to the appropriate anchor moieties. The solid support is then contacted with detection moieties for each of the two *C. difficile* antigens, either separately or as a mixture of the two detection moieties. The solid support can be washed prior to contact with detection moieties to remove unbound reagents. After incubation of the detection moieties for a sufficient time to bind a substantial portion of the immobilized *C. difficile* antigens, any unbound labeled reagents are removed by, for example, washing. The detectable label associated with the detection moieties are then detected. For example, in the case of an enzyme used as a detectable label, a substrate for the enzyme that turns a visible color upon action of the enzyme is placed in contact with the bound detection moiety. A visible color will then be observed in proportion to the amount of the specific antigen in the sample. Where the two anchor moieties are in the same zone of the solid support and two different detection moieties are used, if both antigens are present in the sample, the color of the zone will be a mixture of the colors resulting from the two labels.

In another embodiment, the detection moieties and/or one or more additional components necessary for detection can be added to the sample prior to, or simultaneously with, the contacting of the sample with the solid support. The *C. difficile* toxin A and glutamate dehydrogenase become associated with the detection moieties. This can result in an assay that requires fewer manipulations by the clinician.

Figure 3A:
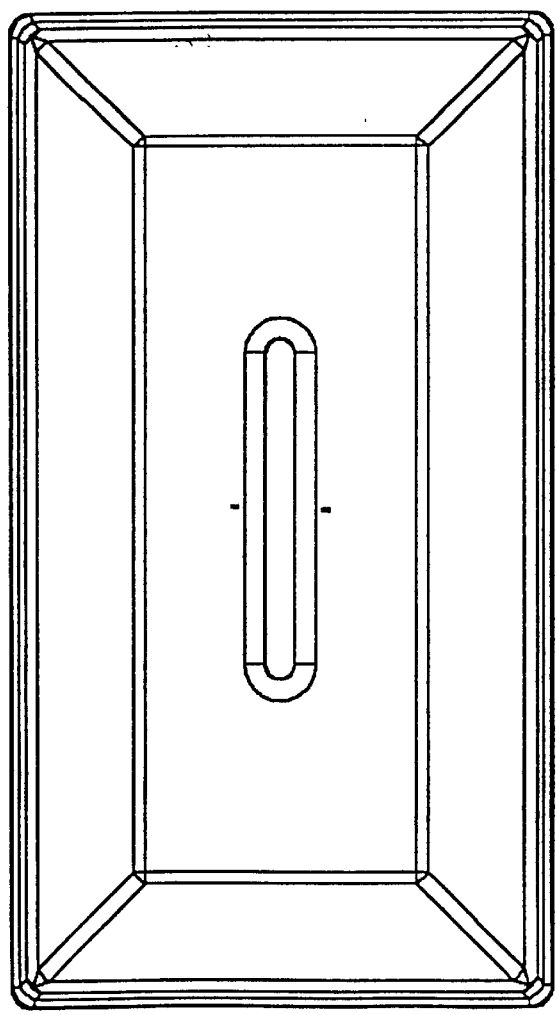
FIGS. 3A–3C show a top piece of an apparatus for performing an immunoassay for simultaneous detection of *C. difficile* glutamate dehydrogenase and toxin A.
Figure 3B:
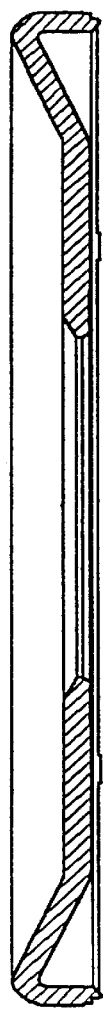
Figure 3C:
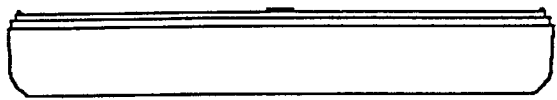

Assay systems for use in the methods and kits of the invention include, but are not limited to, dipstick-type devices, immunochromatographic test strips and radial partition immunoassay devices, and flow-through devices. Conveniently, where the solid support is a membrane, the sample will flow through the membrane, for example, by gravity, capillary action, or under positive or negative pressure. Preferred assay systems for use in the kits and methods of the invention are described in EP 447154. These systems employ an apparatus as shown in FIGS. 3, 4 and 5, which apparatus includes a porous member such as a membrane or a filter onto which is bound a multiplicity of anchor moieties for each of the *C. difficile* antigens, each in a discrete zone. The apparatus also includes a non-absorbent member with a textured surface in communication with the lower surface of the porous member. The textured surface of the non-absorbent member can be a grooved surface such as the surface of a record or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid. In some embodiments, the capillary communication between the porous member and the non-absorbent member favors delaying the transferral of fluid from the porous member to the capillary network formed by the porous member and the textured surface of the non-absorbent member until the volume of the added fluid substantially exceeds the void volume of the porous member. The transferral of fluid from the porous member to the network of capillary channels formed by the porous member and the textured surface of the non-absorbent member can occur without the use of external means, such as positive external pressure or vacuum, or contact with an absorbent material. The devices of the present invention can also include an optional member which is placed in contact with the upper surface of the porous member and may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the non-absorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the sample is added to the porous member, where the sample permeates the void volume of the porous member and thereby contacts the anchor moieties immobilized on the porous member. In a non-competitive assay, the sample to be assayed is applied to the porous member and the respective *C. difficile* antigens, if present, are bound by the anchor moieties. Detection moieties for each *C. difficile* antigen are then added as an additional fluid; these bind to the complex of *C. difficile* antigen and anchor moiety. Alternatively, the detection moieties can be added to the sample prior to application of the sample to the porous member so that the binding of detection moiety to *C. difficile* antigen occurs prior to the binding of *C. difficile* antigen to the anchor moiety. In another embodiment, the anchor moieties and detection moieties are added to the sample, after which the complex of anchor moiety, *C. difficile* antigen, and detection moiety binds to a binding agent that is either combined with these reagents or is immobilized on the porous member. An additional fluid containing reagents to effect a separation of free from bound labeled reagents can be added to remove excess detection moiety, if needed.

This device is designed to provide sufficient sensitivity to measure low concentrations of *C. difficile* toxin A and glutamate dehydrogenase because one can use large amounts of sample and efficiently remove the excess of either or both of *C. difficile* antigen and detection moiety. Indeed, the efficient separation of free from bound label achieved by the network of capillary channels of this device improves the discrimination of specific *C. difficile* antigen-associated signal over non-specific background signal. If needed, a signal developer solution is then added to enable the label of the detection moiety to develop a detectable signal. The signal developed can then be related to the concentration of the target ligand within the sample. In a preferred embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. The point at which the fluid transfer is initiated is dependent upon the objectives of the assay. Normally, it is desirable to contact the sample with all of the zones on the porous member which contain immobilized receptor so that the application of additional fluid effects the separation of unbound label from label which has bound to the porous member. This method enables the detection of the *C. difficile* antigens in a manner that is simple, rapid, convenient, sensitive and efficient in the use of labeled reagents.

Competitive binding assays can also be used to detect *C. difficile* toxin A and glutamate dehydrogenase. Conveniently, these assays are performed using the described devices by adding to a sample a labeled analog of each of the *C. difficile* antigens. The labeled analog and any *C. difficile* antigens present in the sample compete for the binding sites of the anchor moieties. Alternatively, the anchor moieties can be combined with the sample and labeled analogs with subsequent immobilization of the anchor moieties onto the porous member through contact with a binding agent. An additional fluid to separate the free from bound label may be added to the device, followed if needed by a signal development solution to enable detection of the label of the labeled analog which has complexed with anchor moiety immobilized on the porous member. The amount of labeled *C. difficile* antigen analog bound to the porous member is related to the concentration of *C. difficile* antigen in the sample.

This invention also provides kits for the detection and/or quantification of *C. difficile* toxin A and glutamate dehydrogenase by the described methods. The kits can include a container containing one or more of the above-discussed detection moieties with or without labels, and anchor moieties free or bound to solid supports. Also included in the kits can be a suitable membrane, preferably in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include instructions for the use of one or more of these reagents in any of the assays described herein.

The kits of the invention can also include an internal and/or an external control. An internal control can consist of either or both of the *C. difficile* toxin A and glutamate dehydrogenase. The control antigen can conveniently be preattached to the anchor moiety in a zone adjacent to the zone to which the sample is applied. The external control can also consist of either or both of the *C. difficile* toxin A and glutamate dehydrogenase. Typically, the antigen present in the external control will be at a concentration at or above the sensitivity limit of the assay means. The external control antigen can be diluted in the sample diluent and assayed in the same manner as would a biological sample. Alternatively, the *C. difficile* antigen or antigens can be added to an aliquot of an actual biological sample to determine the sensitivity of the assay. The kits of the present invention can contain materials sufficient for one assay, or can contain sufficient materials for multiple assays.

The methods, compositions and kits provided by this embodiment of the invention are capable of detecting *C. difficile* toxin A and/or glutamate dehydrogenase with high sensitivity. The claimed assays and kits will detect *C. difficile* glutamate dehydrogenase when present in a sample at a concentration of about 100 ng/ml or less. Preferably, the detection limit for glutamate dehydrogenase will be about 50 ng/ml or less, more preferably about 10 ng/ml or less, and still more preferably the detection limit for glutamate dehydrogenase will be about 2 ng/ml or less. Similarly, the assays will detect *C. difficile* toxin A when present in a sample at a concentration of about 100 ng/ml or less. Preferably, the detection limit for toxin A will be about 50 ng/ml or less, more preferably about 10 ng/ml or less, and still more preferably the detection limit for toxin A will be about 2 ng/ml or less.

II. High Sensitivity Assays for Toxigenic Strains of *C. Difficile*

Glutamate dehydrogenase is produced by non-toxigenic strains as well as toxigenic strains, while toxin A and toxin B are produced only by toxigenic strains of *C. difficile*. Non-toxigenic strains are considered clinically unimportant because, even if such strains are detected in a sample from a patient, the condition will not progress to pseudomembranous colitis. Therefore, assaying for toxin A or toxin B as well as glutamate dehydrogenase is clinically desirable. However, toxigenic strains of *C. difficile* generally produce toxin A in amounts that can be far less than the amounts of glutamate dehydrogenase produced; toxin B is produced in even smaller amounts. Toxin A production is significantly affected by the environment in which the organism is grown. Because of the low levels of toxin A in many samples, previously existing assays for *C. difficile* toxin A, which generally can detect no less than 2 ng of toxin A per ml, miss approximately 20–30% of the toxigenic *C. difficile* infections. Therefore, if an assay gives a positive result for *C. difficile* glutamate dehydrogenase but is negative for toxin A, it is desirable to perform a second, more sensitive assay for toxin A or toxin B to ensure that the *C. difficile* strain is not actually toxigenic. Similarly, previously known assays for toxin B, such as cytotoxicity assays, are sometimes more sensitive than assays for toxin A but are much less specific. Peterson et al. (1993) *Lab. Diagnos. Infect. Dis.* 7: 277–293; Schleupner et al. (1995) *J. Clin. Microbiol.* 33: 1755–1759. The specificity of cytotoxicity tests can be substantially improved if only samples that are positive for glutamate dehydrogenase are subjected to cytotoxicity testing. Again, a two-step assay such as that provided by the present invention is useful to obtain a more accurate result than is provided by earlier assays. The present invention provides such methods, compositions, and kits for performing such two component tests for toxigenic strains in *C. difficile* . These methods involve the use of an initial assay for *C. difficile* glutamate dehydrogenase, followed by a very high sensitivity assay for *C. difficile* toxin A and/or toxin B that is performed on samples that test positive for glutamate dehydrogenase.

A. Amplification of *C. difficile* Nucleic Acids

Highly sensitive assays for toxin A and/or toxin B that are useful to determine whether a *C. difficile* strain is toxigenic include amplification of a nucleic acid encoding toxin A, toxin B, or a portion thereof, by polymerase chain reaction (PCR), the ligase chain reaction (LCR), the transcription-based amplification system (TAS), the self-sustained sequence replication system (SSR). A wide variety of in vitro amplification methodologies are well-known to persons of skill. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *Chemical & Engineering News*, pp. 36–47; *The Journal Of NIH Research* (1991) 3: 81–94; Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace, (1989) *Gene* 4: 560; and Barringer et al. (1990) *Gene* 89: 117.

Generally, a pair of oligonucleotide primers that specifically hybridize to a nucleic acid encoding a portion of *C. difficile* toxin A or toxin B, or a nucleic acid complementary to such nucleic acid, are allowed to anneal to nucleic acids obtained from a sample, after which the amplification reaction is performed. The presence of an amplified fragment detected by, for example, gel electrophoresis, is indicative that the *C. difficile* strain is toxigenic. Examples of primer pairs that are suitable for amplification of a nucleic acid encoding a portion of *C. difficile* toxin A, toxin B, and glutamate dehydrogenase are found in Example III below. One of skill in the art can ascertain additional primers that are suitable for amplifying nucleic acids that encode *C. difficile* toxin A and/or toxin B and glutamate dehydrogenase. The nucleotide sequences of toxin A (Dove et al., *Infect. Immun.* 58: 480–488 (1990); GenBank Accession No. M30307), toxin B (Barroso et al., *Nucl. Acids Res.* 18: 4004 (1990); GenBank Accession No. X53138), and glutamate dehydrogenase (GenBank Accession No. M65250) are publicly available. To perform the amplification, cells are lysed by, e.g., boiling or other lysis method, after which amplification is performed using reaction conditions known to those of skill in the art. Methods of determining the presence or absence of amplified fragments also are well known to those of skill in the art.

As a positive control, one can also amplify a nucleic acid that is present in toxigenic as well as non-toxigenic *C. difficile* strains. This control amplification can be performed as a separate reaction, or in the same reaction as the amplification of the *C. difficile* toxin A or toxin B. An example of a suitable positive control uses primers that specifically hybridize to a nucleic acid that encodes *C. difficile* glutamate dehydrogenase, or a portion thereof. The presence of an amplified glutamate dehydrogenase nucleic acid fragment is indicative of a successful amplification reaction, and demonstrates that the sample does not contain an inhibitor of the polymerase. If no amplified glutamate dehydrogenase nucleic acid fragment is detected following the amplification reaction, further dilution of the sample may be required to obtain successful amplification.

To detect toxin B as part of the two-component assay, a cytotoxicity assay can also be used. Such cytotoxicity assays are known to those of skill in the art. Although these assays can be quite sensitive at low dilution, specificity is low as many false positives are obtained. By performing the relatively sensitive but nonspecific cytotoxicity assay in conjunction with the glutamate dehydrogenase assay, which eliminates most false positives, a highly accurate assay for toxigenic *C. difficile* is obtained.

B. Magnetic Bead Assays

Additional high sensitivity assays for *C. difficile* toxin A are provided by the present invention. These assays involve the use of magnetic beads to concentrate the toxin A from a sample (see FIG. 2). In summary, these assays are performed by adding a toxin A binding moiety to a sample to be tested for the presence of toxigenic *C. difficile* strains. The toxin A binding moiety and associated toxin A are concentrated by means of a magnetic bead to which is attached a capture moiety that is capable of reversibly binding to the toxin A binding moiety. After the magnetic bead/toxin A binding moiety/toxin A complex is formed, the complex is collected by application of a magnetic field to the sample.

The toxin A binding moiety is capable of specifically binding to *C. difficile* toxin A. For example, a toxin A binding moiety can be a polypeptide such as an antibody, or an antibody fragment, that recognizes *C. difficile* toxin A. Examples of suitable toxin A binding moieties include those described above for use in detection moieties. For example, the hybridoma-produced monoclonal antibody PCG-4, which is described in U.S. Pat. No. 4,533,630, is suitable for use as a toxin A binding moiety. Also useful as toxin A binding moieties are naturally occurring ligands that are specific for toxin A; such ligands can be identified, for example, by affinity chromatography using immobilized toxin A as the affinity reagent. Preferably, the toxin A binding moiety is added to the sample in a sufficient amount and incubated with the sample for a time sufficient for substantially all toxin A in the sample to become associated with the toxin A binding moiety. For example, to 1 ml of a sample, which can be undiluted or diluted (e.g., 1–50 fold or greater dilution), one could add 0.1 to 5 $\mu$g of toxin A binding moiety and incubate for 10 min to 24 hr to obtain nearly complete association of toxin A with the binding moiety.

To concentrate the toxin A/toxin A binding moiety complexes, a magnetic bead to which is attached a capture moiety that specifically binds to the toxin A binding moiety is added to the sample. Magnetic beads or particles, such as magnetic latex beads and iron oxide particles, that are useful in the claimed invention are known to those of skill in the art. For example, magnetic particles are described in U.S. Pat. No. 4,672,040. Magnetic particles are commercially available from, for example, PerSeptive Biosystems, Inc. (Framingham Mass.)., Ciba Coming (Medfield Mass.), Bangs Laboratories (Carmel Ind.), and BioQuest, Inc. (Atkinson N.H.). Coupling of capture moieties to magnetic beads can be accomplished using known methods. For example, beads are commercially available that are derivatized with amino or carboxyl groups that are available for linkage to a protein or other capture moiety using, for example, glutaraldehyde, carbodiimide, diazoto compounds, or other suitable crosslinking reagent. Silanization of magnetically responsive particles provides one method of obtaining reactive groups on the surface of the particles (see, e.g., U.S. Pat. No. 4,672,040 for a description of silanization and silane coupling chemistry). Linking bonds can include, for example, amide, ester, ether, sulfonalmide, disulfide, azo, and others known to those of skill in the art. In one embodiment, the magnetic beads are iron oxide particles that are silanized. An example of suitable silanized beads having functional groups appropriate for covalent linking of capture moieties is the BioMag™ particle that is commercially available from PerSeptive Biosystems, Inc. Although covalent linkage of the anchor moiety to the magnetic bead is generally preferred, noncovalent linkages are also useful in the claimed methods and kits. For example, capture moieties can be attached to magnetic latex beads through noncovalent physical adsorption.

The capture moiety is capable of specifically binding, in a reversible manner, the toxin A binding moiety. Reversible binding between the capture moiety and the toxin A binding moiety can be achieved by attaching to the toxin A binding moiety a molecular tag that is chosen for its ability to specifically and reversibly bind to the capture moiety. The molecular tag and corresponding capture moiety are chosen so that binding of the capture moiety to the molecular tag is reversible under relatively mild conditions. The dissociation conditions are preferably sufficiently mild for the toxin A binding moiety and the toxin A to remain in contact with each other during and after the dissociation step and separation of magnetic beads, so that the toxin A binding moiety and toxin A immediately reassociate upon modification of the solution by, for example, neutralization. More preferably, the toxin A and the toxin A binding moiety remain associated throughout the dissociation and separation steps. By maintaining or immediately reestablishing the association between the toxin A and its binding moiety, the resulting highly concentrated solution containing complexes of toxin A and the toxin A binding moiety can be applied directly to an assay device.

A molecular tag is preferably attached to the toxin A binding moiety by covalent bonding. For example, one method of obtaining a toxin A binding moiety that includes a molecular tag is to use a heterobifunctional linker to link the toxin A binding moiety to the molecular tag. Suitable linkers are known to those of skill in the art. One example of a suitable linker is the heterobifunctional linker SMCC (succinimidyl 4-[N-maleimidomethyl] cyclohexane-1-carboxylate; Sigma Chemical Co., St. Louis, Mo.), which can form a link between a amino residue (for example, lysine) and a thiol (such as that provided by cysteine). Other cross-linkers include, for example, m-maleimidobenzyl-N-hydroxysuccinimide ester (MBS) (Liu et al. (1979) *Biochemistry* 18: 690; Green et al. (1982) *Cell* 28: 477), glutaraldehyde, a carbodiimide succinyl anhydride, N-succinimidyl-3-[2-pyridyldithio]-propionate, and the like.

An additional method by which one can obtain a toxin A binding moiety that includes a peptide molecular tag is to construct a fusion gene in which a nucleic acid that codes for the binding component is operably linked to a nucleic acid that codes for the molecular tag. The nucleic acid encoding the molecular tag is preferably placed at a location in the binding component gene that does not disrupt the ability of the fusion protein obtained to bind to *C. difficile* toxin A. Where the binding component is an antibody, the molecular tag-encoding nucleic acid can be placed at or near the region of the antibody gene that encodes the carboxyl terminus of either the light chain or the heavy chain, or both. Methods for constructing and expressing genes that encode fusion proteins are well known to those of skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

One example of a suitable molecular tag/capture moiety pair is the FLAG™ system (Kodak). The FLAG™ molecular tag consists of an eight amino acid FLAG peptide marker that is linked to the target binding moiety. Conveniently, a target binding moiety having a FLAG™ molecular tag is synthesized by cloning a 24 base pair FLAG coding sequence adjacent to a nucleotide sequence that codes for the target binding moiety and expressing the fusion gene in an appropriate expression vector. The FLAG peptide marker (FIG. 1) also includes an enterokinase recognition site that corresponds to the carboxy-terminal five amino acids. Capture moieties suitable for use with the FLAG peptide marker include antibodies that bind to the FLAG™ peptide. For example, the Anti-FLAG M1, M2 and M5 monoclonal antibodies are commercially available. All eight amino acids of the FLAG peptide marker are required for binding of some anti-FLAG monoclonal antibodies; other antibodies may require fewer amino acids. These anti-FLAG monoclonal antibodies differ in their preference for the location of the FLAG marker peptide relative to the protein it is fused to and in their ability to be bound to or released from the FLAG marker peptide in the presence or absence of calcium. The anti-FLAG M1 (IgG2b) monoclonal antibody binds to the FLAG epitope in the presence of calcium and requires a free amino group on the N-terminal aspartate for high affinity binding. Only the first four amino acids of the FLAG sequence (N-AspTyrLysAsp-C) (SEQ ID NO. 3) are required for anti-FLAG M1 antibody binding; the presence of a-glutamate at the fifth position (AspTyrLysAspGlu) (SEQ ID NO. 4) increases the sensitivity by six-fold (Knappik and Pluckthun (1994) *Biotechniques* 17: 754–761). The anti-FLAG M1 monoclonal antibody is therefore useful as a capture moiety for binding FLAG peptides that are present on the amino terminus of the target binding moiety. One advantage of the anti-FLAG M1 monoclonal antibody as a capture moiety is that because its binding to a FLAG epitope is calcium-dependent, one can the capture moiety from the target binding moiety under extremely mild conditions such as by the addition of a chelating agent such as EDTA. Alternatively, dissociation can be accomplished by competition with FLAG peptide. The anti-FLAG 5 M (IgG1) monoclonal antibody has a high relative affinity for N-terminal Met-FLAG fusion proteins. N-terminal Met-FLAG fusion proteins are created by placing an ATG translational start codon immediately before the FLAG coding sequence. When transfected into an appropriate host, the N-terminal Met-FLAG fusion protein will be expressed in the cytoplasm of the cell. Unlike the anti-FLAG M1 monoclonal antibody, the binding of the anti-FLAG M5 antibody to the FLAG marker peptide is not calcium dependent. Where the target binding moiety is an antibody that includes a FLAG molecular tag, a preferred capture moiety is the anti-FLAG M2 (IgG1) monoclonal antibody, which is also commercially available. This monoclonal antibody binds to the FLAG epitope regardless of its position relative to the remainder of the target binding moiety. Therefore, the FLAG molecular tag can be placed in or near the carboxy terminus of the target binding antibody, thus avoiding disruption of the target analyte binding region. The binding of the anti-FLAG M2 monoclonal antibody is not calcium-dependent, but mild elution of FLAG fusion proteins from anti-FLAG M2 affinity columns can be accomplished by competition with FLAG peptide.

Another example of a suitable molecular tag is a polyhistidine sequence, which is capable of binding to metal chelate affinity ligands. Generally, at least two histidine residues are required to obtain binding to the ligand; the use of additional adjacent histidines increases the binding affinity. Typically, six adjacent histidines are used, although one can use more or less than six. Suitable metal chelate affinity ligands that can serve as the capture moiety for a polyhistidine molecular tag include nitrilo-tri-acetic acid (NTA) (Hochuli, E. (1990) "Purification of recombinant proteins with metal chelating adsorbents" *In Genetic Engineering: Principles and Methods,* J. K. Setlow, Ed., Plenum Press, NY; commercially available from Qiagen (Santa Clarita, Calif.)). Dissociation of polyhistidine sequences from metal chelate affinity ligands can be achieved by bringing the solution containing the magnetic bead-bound complex to a mildly acidic pH such as, for example, pH 4. Also, one can dissociate the binding between the polyhistidine sequence and the metal chelate affinity ligand that comprises the capture moiety by adding to the solution a chelating agent that competes with the molecular tag for binding to the capture moiety. Preferably, the competing chelating agent will have a higher affinity for the capture moiety than does the molecular tag associated with the toxin A binding moiety. Suitable chelating agents include imidazole. Other suitable metal chelate affinity ligands and corresponding methods for dissociation are known to those of skill in the art.

The decapeptide sequence YPYDVPDYAS (SEQ ID NO. 5) and the hybridoma-derived antibody 7F11 are another suitable molecular tag/capture moiety pair. The decapeptide sequence can be attached to the toxin A binding moiety by, for example, attaching a thiol ester to one end of the peptide and attaching the peptide to the toxin A binding moiety by using a suitable heterobifunctional linker such as SMCC. Alternatively, a fusion gene can be constructed in which the reading frames for the decapeptide sequence and the toxin A binding moiety are operably linked. The antibody 7F11, which is a hybridoma-derived monoclonal antibody (deposited under the Budapest Treaty with the American Type Culture Collection (12301 Parklawn Drive, Rockville Md. 20852) on Apr. 3, 1997 and assigned ATCC Accession No. HB-12443) specifically binds to the decapeptide sequence and can be dissociated at pH 10.5 and higher.

To obtain other suitable molecular tag/capture moiety pairs for which binding is reversible under mild conditions, one can screen for peptides that bind a given molecular tag by, for example, enrichment of display libraries, including phage display libraries. A particularly useful method by which to obtain such reversibly binding molecular tag/capture moiety pairs is described in co-filed U.S. patent application Ser. No. 08/832,985, filed Apr. 4, 1997). This method involves enriching conventional display libraries for members displaying more than one copy of a display polypeptide prior to affinity screening of such libraries with a target of interest, such as a molecular tag. The rationale for this method is believed to be that affinity binding of library members to an immobilized target occurs predominantly or exclusively through formation of multivalent bonds between multiple copies of displayed polypeptides on a library member and immobilized target. Accordingly, only members of library displaying multiple copies of a polypeptide are capable of binding to an immobilized target of interest. Conventional libraries typically have a distribution of number of polypeptides per member, in which most members display no copies of a polypeptide, a small proportion display one copy of a polypeptides, a still smaller proportion display two copies, and a still smaller proportion display three or more copies. The methods described in the copending application enrich for the small proportion of conventional display libraries displaying two or more copies of a polypeptide. It is this rare fraction of conventional libraries that is capable of specific binding to an immobilized target.

Enrichment can be achieved by the inclusion of a marker as a component of the fusion protein from which polypeptides are displayed. The marker can be any polypeptide with a known receptor showing high binding specificity for the marker. The same marker is included in each member of the library. Enrichment is effected by screening the library for affinity binding to an immobilized receptor for the marker. Only library members having two copies of the marker are capable of binding to the immobilized receptor. By implication, library members having two copies of the marker have two copies of the fusion protein containing the marker, and two copies of a polypeptide to be screened. The library members that bind to the receptor thus constitute the small subpopulation of library members displaying two or more polypeptides. The library members not binding to the receptor are the majority of library members which display fewer than two copies of a polypeptide (i.e., zero or one copy). These library members, which would nonspecifically bind to the immobilized target in subsequent steps without contributing any members capable of specific binding, can thus be substantially eliminated.

After dissociation of the bound library members from the marker-specific receptor, these enriched library members, which display multiple copies of polypeptide, can then be subjected to one or more rounds of affinity screening to any immobilized target of interest. Because most library members that would otherwise contribute to nonspecific binding have been eliminated before affinity screening to the target, each round of affinity screening typically results in a greater enrichment for library members with affinity for the target than would be the case in conventional methods. The greater degree of enrichment per round of screening allows adequate screening to be accomplished in fewer rounds and/or a greater proportion of the repertoire of specifically binding library members to be identified.

So efficient are these selection methods that they result in diverse populations in which the vast majority of members retaining full-length coding sequences encode polypeptides having specific affinity for the target of interest, such as the molecular tag. These polypeptides may differ in fine binding specificity within the target and binding affinity for the target. Thus, one can use these methods to identify polypeptides that bind to the target in a manner that is reversible under mild conditions. This procedure involves the use of the target of interest as the affinity reagent. Binding is allowed to proceed to equilibrium and then the target is brought out of solution by contacting with a solid phase in a process known as panning (Parnley & Smith, *Gene* 73, 305–318 (1988)). Library members that remain bound to the solid phase do so by virtue of polyvalent bonds between them and target molecules. Unbound library members are washed away from the solid phase. Bound members are then dissociated from the solid phase (e.g., by change of ionic strength or pH). Members that are dissociated under relatively mild conditions such as, for example, a change in ionic strength or pH, or addition of a substance that competes with the tag for binding to the receptor, are then collected and used as capture moieties. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The dissociated library members are now enriched for two features: multivalent display of polypeptides and display of polypeptides having specific affinity for the target of interest. These library members can be subjected to further round(s) of affinity screening to the target without amplification. Alternatively, the library members can be amplified (e.g., by reinfection of bacteria and harvesting of progeny for a phage display library) to produce a secondary library. The secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been performed.

The library members can also be used to obtain polyclonal capture moieties. The use of polyclonals has a number of advantages with respect to monoclonals. By binding to multiple sites on a target, polyclonal antibodies or other polypeptides can generate a stronger signal (for diagnostics) or greater blocking/inhibition/cytotoxicity (for therapeutics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. Methods for obtaining polyclonals are described in co-filed U.S. patent application Ser. No. 08/832,985 (filed on Apr. 4, 1997.In these methods, the nucleic acid sequences encoding displayed polypeptides such as are produced by the above methods can be subcloned directly into an expression vector without clonal isolation and testing of individual members. Generally, the sequence encoding the outer surface protein of the display vector fused to displayed polypeptides is not excised or amplified in this process. Once expressed in a suitable host cell, collections of antibodies or other polypeptides are purified from culture media and host cells. Usually, polypeptides are expressed with signal sequences and are thus released to the culture media. However, if polypeptides are not naturally secreted by host cells, the polypeptides can be released by treatment with mild detergent. Polypeptides can then be purified by conventional methods including ammonium sulfate precipitation, affinity chromatography to immobilized target, column chromatography, gel electrophoresis and the like (see generally Scopes, *Protein Purification* (Springer-Verlag, N.Y., 1982). These polypeptides can then be linked to magnetic beads as described below.

Other moieties are known that reversibly and specifically bind to an agent that is useful as a capture moiety. For example, certain derivatives of biotin such as 2-iminobiotin are available that bind to avidin in a pH-sensitive manner. Orr, G. (1981) *J. Biol. Chem.* 256: 761–766; commercially available from Pierce Chemical Co., Rockford Ill. This biotin derivative can be attached to the toxin A binding moiety as a molecular tag, while avidin is attached to the magnetic bead and serves as the capture moiety. To bind the toxin A binding moiety to the capture moiety, the sample and components are incubated at a pH of at least about 9, typically between pH 9–11, at which pH avidin strongly interacts with 2-iminobiotin. After concentration using a magnetic field, the toxin A binding moiety and bound toxin A are dissociated from the magnetic bead by adjusting the pH to about 6 or less and/or by adding biotin to the sample. Other examples of suitable molecular tags are known in the art.

To facilitate detection of toxin A after concentration using the described method, the toxin A binding moiety will also generally include a hapten or other group to which a detection moiety is capable of binding. The molecular tag can serve this function, or the toxin A binding moiety can be linked to a separate group, preferably by a covalent linkage. Suitable haptens are known to those of skill in the art and are described, for example, in the *Handbook of Fluorescent Probes and Research Chemicals* ($6^{th}$ Ed., Molecular Probes, Inc., Eugene Oreg.). For example, dinitrophenol (DNP), digoxigenin, barbiturates (see, e.g., U.S. Pat. No. 5,414, 085), and several types of fluorophores are useful as haptens, as are derivatives of these compounds. Haptens are used in conjunction with a detection moiety that includes an antibody or other moiety that specifically binds to the particular hapten. Other groups that are useful for binding of the detection moiety include biotin, which is bound by a detection moiety that comprises avidin. Kits are commercially available for linking haptens and other moieties to proteins and other molecules. The molecular tag and hapten can be attached to the toxin A binding moiety simultaneously in the same reaction mixture. For example, where both the molecular tag and the hapten include a thiol, a heterobifunctional linker such as SMCC can be used to attach the molecular tag and the hapten to lysine residues present on the toxin A binding moiety. Preferably, the toxin A binding moiety will include multiple molecular tags and haptens. By choosing the ratio of hapten to molecular tag present in an attachment reaction, one can control the ratio of hapten to molecular tag present on the toxin A binding moiety. Typically, the number of haptens attached to a toxin A binding moiety will be greater than the number of molecular tags; for example, suitable ratios of hapten: molecular tag include 2:1, 5:3, and the like.

The magnetic bead and associated capture moiety can be added to the sample before, after, or simultaneously with the toxin A binding moiety. Preferably, the magnetic beads are added to the sample in an amount and for a length of time sufficient for substantially all of the toxin A binding moiety, and associated *C. difficile* toxin A, to become bound to the capture moiety. For example, to a 40 ml sample that was either undiluted or diluted 1–50-fold or more, one could add between 1 mg and 20 mg of magnetic beads. In a preferred embodiment, about 400 $\mu$l of BioMag (1% solids) is used. The amount of beads added is inversely proportional to the time required to obtain substantially complete association of the toxin A binding moiety with the capture moiety.

After the toxin A binding moiety, toxin A, and the capture moiety have become associated into a magnetic bead-bound complex, a magnetic field is applied to the sample to collect the magnetic bead-bound complex. For example, the container containing the sample can be placed in the presence of a pole face of a permanent magnet, thus drawing the magnetic bead-bound complexes to an inner surface of the container. The unbound portion of the sample can then be removed by, for example, aspiration or by pouring from the container while the container remains in the presence of the magnetic field. Optionally, the magnetic bead-bound toxin A complex can then be washed, after which the container is returned to the magnetic field for re-collection of the magnetic bead-bound complex.

The use of capture moieties and toxin A moieties that are capable of binding in a reversible manner provides a significant advantage over previously known assays. In earlier assays, a target analyte that had been concentrated by use of magnetic beads would generally be detected while still associated with the beads. The sensitivity of such methods was limited by nonspecific binding. As a sufficient number of beads were added to a sample to bind all or most of the analyte in the sample, the nonspecific binding to the beads increased, thus decreasing sensitivity. If fewer beads were used to decrease nonspecific binding, the sensitivity would also decrease because less than substantially all of the target analyte would be captured. Thus, the signal to noise ratio of these assays was relatively constant, placing a limit on sensitivity. For clinical diagnosis of toxigenic *C. difficile* infection, earlier methods would not provide sufficient sensitivity to ensure that no *C. difficile* strains are incorrectly diagnosed as being non-toxigenic.

The present invention solves this sensitivity problem by dissociating the toxin A binding complex and associated toxin A from the magnetic bead prior to the detection step. Because the magnetic beads are removed prior to detection, nonspecific binding due to the beads is eliminated. Therefore, a greater amount of beads can be used in the concentration step, ensuring that essentially all of the toxin A present in a relatively large sample volume is captured. For example, one can use 100-fold more magnetic beads using the present invention compared to microtiter assays that were previously known. The claimed assay for *C. difficile* toxin A is highly sensitive, being able to detect levels of toxin A in a sample as low as 1 ng/ml. Preferably, the assay is able to detect 0.1 ng/ml or less toxin A, and most preferably the sensitivity is greater than about 0.01 ng/ml toxin A.

The reduction in nonspecific binding achieved by use of reversibly associating capture moieties and toxin A moieties makes possible the use of various methods to detect the presence of toxin A. For example, an immunoassay procedure is conveniently used. Often, it is desirable to immobilize the toxin A on a solid support as part of the detection step. For example, after removing the magnetic beads from the solution containing the concentrated toxin A, the solution can be applied to a solid support upon which is immobilized an anchor moiety that specifically binds to an epitope of *C. difficile* toxin A (see FIG. 2). The epitope to which the anchor moiety binds can be the same as or different than the toxin A epitope to which the toxin A binding moiety binds. Suitable anchor moieties include those that are described above for use in the combined *C. difficile* toxin A and glutamate dehydrogenase assay. A detection moiety that is specific for the toxin A binding moiety or to a hapten attached to the toxin A binding moiety is also applied to the solid support, after which unbound reagents are removed by washing and the presence or absence of the detectable label is determined by methods appropriate for the particular label employed.

This invention also provides kits for detecting the presence of toxigenic strains of *C. difficile* toxin A using magnetic beads as described herein. The kits can include a container that contains a toxin A binding moiety that specifically binds to *C. difficile* toxin A, a magnetic bead to which is attached a capture binding moiety that specifically and reversibly binds to the toxin A binding moiety, a solid support upon which is immobilized an anchor moiety that specifically binds to at least one epitope of *C. difficile* toxin A, and a detection moiety that is conjugated to a detectable label and specifically binds to the toxin A binding moiety or to a hapten present on the toxin A binding moiety. The anchor moiety can be the same as or different than the toxin A epitope to which the toxin A binding moiety binds. Conveniently, the solid support can be mounted in an assay device such as that described above. Preferably, the kits will also include reagents used in the described assays, including reagents useful for detecting the presence of the detectable label. Other materials useful in the performance of the assays can also be included in the kits, including test tubes, magnets, transfer pipettes, and the like. Kits can contain materials sufficient for one assay, or can contain sufficient materials for multiple assays. The kits can also include instructions for the use of one or more of these reagents in any of the assays described herein.

The kits of the invention can also include an internal and/or an external control. An internal control can consist of *C. difficile* toxin A. The control antigen can conveniently be preattached to the anchor moiety in a zone adjacent to the zone to which the sample is applied. The external control can also consist of *C. difficile* toxin A. Typically, the antigen present in the external control will be at a concentration at or above the sensitivity limit of the assay means. The external control antigen can be diluted in the sample diluent and assayed in the same manner as would a biological sample. Alternatively, the *C. difficile* antigen or antigens can be added to an aliquot of an actual biological sample to determine the sensitivity of the assay.

The present invention also provides highly concentrated preparations that include *C. difficile* toxin A and a toxin A binding moiety. These preparations are prepared using the methods described above which involve reversible binding of the toxin A binding moiety to a capture moiety that is linked to a magnetic bead. The concentration of toxin A in the claimed concentrated preparations is typically at least about 2-fold greater than the toxin A concentration in the test sample from which the concentrated preparation was prepared. More preferably, the concentrated preparation will be at least about 10-fold more concentrated, and most preferably at least about 100-fold more concentrated than the test sample.

III. Glutamate Dehydrogenase Assay for Toxigenic *C. difficile* Strains

A further embodiment of the present invention provides compositions, methods, and kits for detecting the presence of toxigenic *C. difficile* strains in a test sample by performing an assay for *C. difficile* glutamate dehydrogenase. This aspect of the invention is based upon the discovery that a high percentage of samples that test positive for *C. difficile* glutamate dehydrogenase but negative for toxin A and/or toxin B are nevertheless toxigenic. Experiments described in Example III found that fourteen of seventeen randomly selected samples that tested positive for glutamate dehydrogenase and negative for toxin A by immunoassay were actually toxigenic. These results demonstrate that the failure to detect toxin A and/or toxin B in these samples is due to insufficient assay sensitivity, rather than to an absence of toxigenic *C. difficile* in the sample.

These results also demonstrate that a very high percentage of *C. difficile* found in biological samples is toxigenic. Therefore, for clinical purposes, a positive result in a glutamate dehydrogenase assay is sufficient to conclude that the sample contains toxigenic *C. difficile*. Toxin A and/or toxin B need not be assayed directly in order to reach this conclusion. However, previously available assays for *C. difficile* glutamate dehydrogenase lacked sufficient sensitivity to accurately diagnose *C. difficile* infection. The present invention provides more sensitive assays for *C. difficile* glutamate dehydrogenase that increase the accuracy of *C. difficile* infection determinations. While approximately 90% of tests for *C. difficile* using previously available assays yield a negative result, the more sensitive assays provided by the instant invention are capable of detecting a substantial number of additional positive samples. These additional cases of toxigenic *C. difficile* infection would have gone undetected, often with very undesirable consequences, prior to the claimed invention.

The highly sensitive assay means for detecting *C. difficile* glutamate dehydrogenase are, in one embodiment, binding assays. In these assays, which include immunoassays, glutamate dehydrogenase is detected using a detection moiety that is capable of specifically binding to the *C. difficile* glutamate dehydrogenase. The detection moiety include at least a binding component and a detectable label. Suitable binding components, which include any moiety that is capable of specifically binding to the *C. difficile* glutamate dehydrogenase, can be those that are discussed above for the combined glutamate dehydrogenase/toxin A assays.

For clinical diagnosis of *C. difficile* infection, a preferred format for use of the claimed methods involves detecting *C. difficile* glutamate dehydrogenase after immobilization on a solid support. Such assays are described above for the combined glutamate dehydrogenase/toxin A assays. A preferred anchor moiety that specifically binds to *C. difficile* glutamate dehydrogenase is the recombinant polyclonal antibody CD.43.5.PC.

The glutamate dehydrogenase assays provided by the invention are more sensitive than those previously used in the clinic. Previously available assays include a latex agglutination assay, which has a sensitivity of approximately 400 ng/ml, and another more rapid test (ImmunoCard™ *C. difficile* test, Meridian Diagnostics, Inc., Cincinnati Ohio) that has a sensitivity of about 125 ng/ml. In contrast, the assays provided by the invention can detect *C. difficile* glutamate dehydrogenase at levels of 100 ng/ml or less, more preferably the sensitivity is about 10 ng/ml or less, still more preferably about 2 ng/ml or less, and most preferably the assays can detect *C. difficile* glutamate dehydrogenase at a concentration of about 1 ng/ml or less. Because *C. difficile* typically produces glutamate dehydrogenase in amounts that are about 100-fold greater than the amount of toxin A produced, the highly sensitive assays for *C. difficile* glutamate dehydrogenase provided by the invention are equivalent in sensitivity to assays for toxin A that have a sensitivity of about 0.01 ng/ml or less.

EXAMPLES

The following examples are offered to illustrate, but not to limit the present invention.

I. Simultaneous Assay of *C. difficile* Toxin A and Glutamate Dehydrogenase

A. Preparation of Antibody-alkaline Phosphatase Conjugates for use as Detection Moieties Detection moieties for use in the assay were prepared by conjugating alkaline phosphatase to antibodies for the respective *C. difficile* antigens. The recombinant polyclonal antibody CD.TXA.1.PC was used to detect toxin A, while CD.43.9 was used for detection of glutamate dehydrogenase. Both antibodies were prepared as described in co-filed patent application U.S. Ser. No. 08/832,985, filed Apr. 4, 1997). Alkaline phosphatase (AP, Calzyme Laboratories, San Luis Obispo, Calif.) was dialyzed against a minimum of 100 volumes of column buffer (50 mM potassium phosphate, 10 mM borate, 150 mM NaCl, 1 mM $MgSO_4$, pH 7.0) at 2–8° C. for a minimum of four hours and the buffer was changed at least twice prior to use of the AP. After the AP was removed from dialysis and brought to room temperature, the concentration was determined by determining the $A_{280}$, with an absorbance of 0.77 indicating a 1 mg/ml solution. The AP was diluted to 5 mg/ml with column buffer.

For crosslinking the AP to the antibody, AP was first linked to succinimidyl 4-(N-maleimidomethyl cyclohexane-1-carboxylate (SMCC, Pierce Chemical Co., Rockford Ill.) using a 20:1 ratio of SMCC:AP. SMCC was dissolved in acetonitrile at 20 mg/ml and diluted by a factor of 84 when added to AP while vortexing or rapidly stirring. The solution was allowed to stand at room temperature for 90 minutes before the unreacted SMCC and low molecular weight reaction products were separated from the AP using gel filtration chromatography (G50 Fine, Pharmacia Biotech, Piscataway, N.J.) in a column equilibrated with column buffer.

Recombinant antibodies were reacted with 1 mM dithiothreitol (DTT, Calbiochem, San Diego, Calif.) for 30 minutes at room temperature to reduce a cysteine residue present near the carboxy terminus of the heavy chain constant region. The DTT was separated from the antibody by gel filtration chromatography using G50 Fine in column buffer without $MgSO_4$ but containing 0.1 mM ethylenediaminetetraacetic acid (EDTA, Fisher Scientific, Pittsburgh, Pa.). The AP and the antibody were mixed together in a molar ratio of 6 antibodies to one alkaline phosphatase and the conjugation reaction was allowed to continue for one hour at room temperature. To stop the conjugation, 2-mercaptoethanol was added to 1 mM final concentration to the conjugate solution and reacted for 5 minutes followed by the addition of N-ethyl maleimide to 2 mM final concentration. The conjugate was purified by gel filtration chromatography using an acrylamide-based gel filtration medium such as SEHACRYL™ S-200 HR (Pharmacia Biotech, Piscataway, N.J.). The free antibody was excluded from the conjugate pool which was diluted for use in immunoassays in a conjugate diluent containing 1% bovine serum albumin (from 30% BSA, Bayer, Kankakee. Ill.), 2% casein (Hammersten grade, Research Organics, Cleveland, Ohio), 100 mM trehalose (Aldrich Chemical Co., Milwaukee, Wis.), 50 mM potassium phosphate, 150 mM sodium chloride, 1 mM MgSO4, 0.1 mM $ZnCl_2$, 0.1% polyvinyl alcohol (80% hydrolyzed, Aldrich Chemical Co., Milwaukee Wis.), pH 7.0.

B. Preparation of Antibody-casein Conjugates for use as Anchor Moieties

Anchor moieties for the *C. difficile* glutamate dehydrogenase were prepared as follows. Where recombinant antibodies were used as anchor moieties, the antibodies were first conjugated to casein. Casein was dissolved in deionized water at 2.5% solids by stirring it at 37–45° C. while adding concentrated potassium hydroxide to keep the pH of the solution between 7 and 8. After the pH had stabilized at 7.0, the casein was diluted with column buffer containing 50 mM potassium phosphate, 10 mM borate, 150 mM sodium chloride, 0.1 mM EDTA, pH 7.0, to a final $A_{280}$ of 10. A solution of SMCC was prepared at 20 mg/ml (60 mM) in acetonitrile; this was diluted into the casein solution to a final concentration of 2 mM SMCC. The solution was allowed to stand for 90 minutes at room temperature and then was subjected to gel filtration chromatography in a column containing G50 Fine equilibrated in column buffer in order to separate the protein from the reactants. The casein was mixed with recombinant antibody that had been reacted with 1 mM DTT and subjected to gel filtration chromatography to remove the DTT as described in Example I-A above. The antibody was mixed with the casein in a 4:1 molar ratio and the reaction was allowed to proceed for one hour at room temperature before the conjugation was stopped as described above. The conjugate solution was subjected to gel filtration chromatography in a column containing Sephacryl S-200 HR in order to separate the conjugated antibody from the unconjugated antibody. The conjugated antibody was concentrated using an ultrafiltration membrane and subjected to dialysis vs. borate-buffered saline (BBS, 20 mM borate, 150 mM sodium chloride, 0.02% sodium azide, pH 8.2) and stored in BBS until immobilization on nylon membranes.

C. Preparation of Assay Devices

The assays were performed using anchor moieties that were immobilized on nylon membranes. Intact IgG antibodies were immobilized directly, while recombinant Fab antibodies were conjugated to casein as described above prior to immobilization. The antibodies were immobilized on the nylon membranes (5 µm pore size; Immunodyne™, Pall Corporation, Glen Cove, N.Y.) in a continuous process by pumping an antibody solution directly onto the membrane while the membrane was moved past a stationary nozzle which dispensed the antibody solution at a flow rate controlled by the pump. The antibody solution typically contained antibody at a concentration between 1 and 20 mg/ml in a buffer containing 20 mM borate, 150 mM sodium chloride, 0.02% sodium azide, and 10% trehalose, pH 8.2.

Each antibody was immobilized in a line approximately 0.040 inches wide, such that approximately 36 μL of antibody solution was required per linear foot of membrane. The antibody solution applied to the membrane was dried prior to blocking the entire membrane by saturating it with a solution containing 2% casein, 40% an immunossay stabilizer such as STABILCOAT™ (Bio-metric Systems, Eden Prairie, Minn.), 0.25% t-octylphenoxypolyethoxyethanol (TRION X-100™) (Sigma Chemical Co., St. Louis, Mo.) and drying the membrane in a drying tunnel or in a dry room. The antibody can also be applied in spots by applying a volume of approximately 1 μL of antibody solution to the membrane at the desired location prior to blocking and drying the membrane. Generally, several lines of immobilized antibody were placed on a membrane in this manner and the membrane was cut perpendicular to the direction of the antibody lines for placement in the assay devices.

The cut membrane pieces were ultrasonically welded to an opening in a plastic device top (see FIG. 3A—top view, FIG. 3B—side section, and FIG. 3C—end view) which was then ultrasonically welded to a plastic bottom piece (see FIG. 4A—top view, FIG. 4B—side section, and FIG. 4C—end view) having grooves cut into its upper surface. The contact between the membrane and the two plastic pieces resulted in a network of capillary channels that caused fluids added to the membrane to flow through the membrane and into the capillary network between the two plastic pieces. Such devices are described in European Patent Application No. 447154.

For the immunoassay of toxin A and glutamate dehydrogenase in the same device, a total of five lines of antibody were immobilized on the membrane. The top two lines in the device were positive controls for the immunoassay of toxin A and glutamate dehydrogenase respectively. The antibody solution used in the immobilization step for the toxin A positive control contained toxin A at 1 μmg/ml mixed with the PCG-4 antibody for toxin A at 1 mg/ml, together with an additional 10 mg/ml of bovine IgG. For the glutamate dehydrogenase positive control, the antibody solution used for immobilization contained 1 μg/ml of glutamate dehydrogenase mixed with approximately 10 μg/ml of CD.43.5.PC antibody conjugated to casein, together with an additional 10 mg/ml of bovine IgG. The next two lines on the membrane were for the capture and detection of toxin A and glutamate dehydrogenase, respectively. The antibody solution used to immobilize the antibody for toxin A contained the PCG-4 antibody at 20 mg/ml. The antibody solution used to immobilize the antibody for glutamate dehydrogenase contained approximately 2 mg/ml of the CD.43.5.PC antibody conjugated to casein. The last line of immobilized antibody on the device was a negative control line; the antibody solution used to apply this line to the membrane contained a monoclonal antibody (20 mg/ml) that was specific for an antigen not found in *C. difficile*.

For filtering samples prior to performing the assays, disposable filter devices were constructed using standard 10-cc plastic syringes. Disks of filter material were cut to a diameter that would allow the disk to be placed into the barrel of the syringe so that sufficient contact was created between the syringe barrel and the edge of the filter disk. This prevented fluids from bypassing the filter material when liquid samples were forced through the filter by the plunger. At the bottom of the syringe closest to the outlet was a disk of porous plastic (Porex Technologies, Fairburn, Ga.). The next two disks of filter material were both cut from CELLUPORE™ cellulose fiber-containing filter grade 850 material (Cellulo Co., Fresno, Calif.). The next disk of filter material was cut from CELLUPORE™ filter grade 315 material (Cellulo Co., Fresno, Calif.). The final filter element in the syringe barrel was a wad of glass wool that served as a prefilter for the filter elements described previously. An additional filter element that was used was a 13 mm syringe filter containing a glass microfiber (GMF) filter with a rating of 0.45 μm (Whatman, Clifton, N.J.). The syringe filter was placed on the outlet of the syringe so that samples passing through the filter elements in the barrel of the syringe were forced through the syringe filter before being collected in a tube. An alternative filter device that contains essentially the same elements is the Autovial™ (Whatman, Clifton, N.J.) which is a disposable syringe that has a GMF glass fiber filter with a rating of 0.45 μm already connected to the end of the syringe. The other filter elements described above are also present in the barrel of the Autovial in the same order.

D. Simultaneous Immunoassay of Glutamate Dehydrogenase and Toxin A

Stool samples (approximately 0.5g or 0.5 ml) were diluted tenfold with sample diluent containing 1% casein, 100 mM potassium phosphate, 150 mM sodium chloride, 0.1% Dow 193 (dimethyl, methyl(polyethylene oxide) siloxane (78 wt %), polyethylene oxide monoallyl ether (14 wt %), and polyethyle glycol (7 wt %)) surfactant (Dow Corning, Midland, Mich.), 0.1% bovine IgG (Sigma Chemical Co., St. Louis, Mo.), 0.1% sodium azide, pH 7.0, and then poured into the barrel of a filter device. The syringe plunger was inserted into the filter device and pressed down to expel the filtered sample through the end of the syringe into a tube. Using a disposable transfer pipet, 0.6 ml of sample was taken from the tube and transferred to the exposed membrane in the immunoassay device described above.

After the sample drained through the membrane in the device, a mixture of antibodies conjugated to alkaline phosphatase was applied in a volume of 140 μL and incubated for 3 minutes. The mixture of conjugates contained an antibody specific for toxin A (CD.TXA.1.PC) and an antibody specific for glutamate dehyrogenase (CD.43.9), both are described in co-filed U.S. patent application Ser. No. 08/832,985 (filed on Apr. 4, 1997). Both antibodies were present in the mixture at approximately 10 μg/ml in conjugate diluent described above. After the incubation, six drops of wash solution containing 100 mM tris (hydroxymethyl) aminomethane (TRIS, Fisher Scientific, Pittsburgh, Pa.), 150 mM sodium chloride, 0.5% Dow 193 surfactant, 0.1% sodium azide, and 20 mg/l of NBT were applied from a dropper bottle. After the wash drained into the membrane, another six drops of wash solution were applied and allowed to drain. Three drops of substrate solution containing 10 mM indoxyl phosphate (JBL Scientific, San Luis Obispo, Calif.), 200 mM 2-amino-2-methyl-1-propanol (JBL Scientific, San Luis Obispo, Calif.), 500 mM TRIS, pH 10.2, were added from a dropper bottle and the device was incubated for five minutes at room temperature.

At the end of the incubation time, the presence of any visually detectable purple to black lines was noted. The positive control zones described above developed clearly visible lines that resulted from the binding of the antibody-alkaline phosphatase conjugates to the immobilized complexes of either toxin A and PCG-4 or glutamate dehydrogenase and CD.43.5.PC. Control samples containing toxin A or glutamate dehydrogenase spiked from purified preparations of these proteins to concentrations of 2 ng/ml or greater resulted in visible lines at the respective zones for the detection of these proteins. Glutamate dehydrogenase was prepared using an expression vector containing a gene encoding the enzyme; the complete nucleotide sequence is available in GenBank, Accession No. M65250. Toxin A was obtained from TechLab, Blacksburg Va. The negative control zone for the detection of non-specific binding of reagents that results in color development did not develop any visible response during any of the assays described. Testing of clinical samples yielded results that were either negative (no visible lines at detection zones for toxin A or glutamate dehydrogenase), positive for glutamate dehydrogenase only (visible line at detection zone for glutamate dehydrogenase, no visible line at detection zone for toxin A), or positive for both toxin A and glutamate dehydrogenase (visible lines at both detection zones).

The performance of the simultaneous assay for toxin A and glutamate dehydrogenase was compared to a commercially available microtiter plate sandwich assay for toxin A (Premier, Meridian Diagnostics, Cincinnati Ohio). A total of 46 specimens were obtained from either a hospital laboratory or a reference laboratory and were tested by both methods. Toxin A was detected in 6 of 46 specimens by the method described herein, and glutamate dehydrogenase was detected in 23 of 46 specimens. Every specimen positive for toxin A was also positive for glutamate dehydrogenase. The microtiter plate assay for toxin A detected 7 positive samples, 2 of which were not detected by the method of the present invention for toxin A but which were positive using the glutamate dehydrogenase method of the present invention. Sixteen samples were positive by the glutamate dehydrogenase method of the present invention but negative by the microtiter plate assay for toxin A.

II. High-Sensitivity Assay for *C. difficile* Toxin A using Magnetic Beads

This assay used magnetic beads to concentrate *C. difficile* toxin A from a sample prior to detecting the toxin A by sandwich assay. A schematic of the assay strategy is shown in FIG. 2.

A. Preparation of Monoclonal Antibodies 7F11 and 3E12

1. Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetylimidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroformhexane to afford 4.8 g (41% yield) acetylthiopropionic acid as a white solid with a melting point of 44–45° C.

2. Decapeptide and Barbiturate Derivatives

The decapeptide, YPYDVPDYAS (SEQ ID NO. 5), (Chiron Mimotopes Peptide Systems, San Diego, Calif.) was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 minutes at room temperature. This solution was added to the decapeptide solution and the reaction mixture was stirred for at least six hours at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and flitered using a fine fritted Buchner funnel. The solid was washed with an additional 20 mL of methylene chloride and the Buchner funnel was dried under vacuum. In order to hydrolyze the derivative to generate a free thiol, it was dissolved in 70% DMF and 1 N potassium hydroxide was added to a final concentration of 0.2 N while mixing vigorously. The derivative solution was allowed to stand for 5 minutes at room temperature prior to neutralization of the solution by the addition of a solution containing 0.5 M potassium phosphate, 0.1 M borate, pH 7.0, to which concentrated hydrochloric acid has been added to a final concentration of 1 M. The thiol concentration of the hydrolyzed decapeptide derivative was determined by diluting 10 $\mu$L of the solution into 990 $\mu$L of a solution containing 0.25 mM 5,5'-dithiobis (2-nitrobenzoic acid) (DTNB, Aldrich Chemical Co., Milwaukee Wis.) and 0.2 M potassium borate, pH 8.0. The thiol concentration in mM units was equal to the $A_{412}$(100/13.76). The barbiturate derivative was prepared as described in U.S. Pat. No. 5,414,085, Example 3.

3. Preparation of Conjugates of Barbiturate Derivative and Decapeptide Derivative with Keyhole Limpet Hemocyanin and Bovine Serum Albumin Keyhole limpet hemocyanin (KLH, 6 ml of 14 mg/ml, Calbiochem, San Diego, Calif.) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The hydrolyzed barbiturate derivative and the hydrolyzed decapeptide derivative were separately added to portions of the KLH-maleimide in substantial molar excess over the estimated maleimide amounts present and the solutions were stirred for 4 hours at 4° C. and then each was dialyzed against 3 volumes of one liter of pyrogen-free phosphate-buffered saline, pH7.4, prior to immunization.

Bovine serum albumin (BSA, 3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The hydrolyzed barbiturate derivative and the hydrolyzed decapeptide derivative were separately added to portions of the BSA-maleimide in substantial molar excess over the estimated maleimide amounts present and the solutions were stirred for 4 hours at 4° C. The solutions were used to coat microtiter plates for the detection of antibodies that bound to either the barbiturate derivative or the decapeptide derivative by standard techniques.

4. Production of Hybridomas and Primary Selection of Monoclonal Antibodies

Immunization of Balb/c mice was performed according to the method of Liu, D., Purssell, R., and Levy, J. G., *Clin. Chem.*, 25: 527–538 (1987). Fusions of spleen cells with SP2/0-Ag 14 myeloma cells, propagation of hybridomas, and cloning were performed by standard techniques. Selection of hybridomas for further cloning began with culture supernatant at the 96-well stage. A standard ELISA procedure was performed with BSA conjugates of either barbiturate derivative or decapeptide derivative adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not linked to either derivative identified which of the positive clones that bound the BSA conjugates were actually binding the SMCC-BSA. The antibodies specific for SMCC-BSA may be eliminated at this step. Monoclonal antibodies 7F11, specific for the decapeptide derivative, and 3E12, specific for the barbiturate derivative, were produced and selected by this process. Cells that produce each of these antibodies have been deposited under the Budapest Treaty with the American Type Culture Collection (12301 Parklawn Drive, Rockville Md. 20852) on Apr. 3, 1997, and have been assigned ATCC Accession Nos. ATCC HB-12443 (7F11) and ATCC HB-12442 (3E12).

B. Preparation of Detection Moiety

The recombinant antibody 3E12 was used to construct the detection moiety. This antibody, which binds specifically to a barbiturate derivative that was attached to the toxin A binding moiety as a hapten, was conjugated to alkaline phosphatase by a procedure similar to that described in I-A above. Intact IgG antibody 3E12 was reacted with succinimidyl 3-(2-pyrridyldithio)propionate (SPDP, Molecular Probes, Eugene, Oreg.) using antibody at 10 mg/ml and a ratio of 10:1 SPDP:antibody in a buffer containing 50 mM potassium phosphate, 10 mM borate, 150 mM sodium chloride, pH 7.0, for 90 minutes at room temperature. The reaction was stopped by adding aminoethanesulfonic acid (Sigma Chemical Co., St. Louis, Mo.) to a final concentration of 20 mM. The reagent DTT was added to 2 mM final concentration and the reduction was allowed to proceed for 30 minutes at room temperature. The antibody was separated from the low molecular weight reactants by gel filtration chromatography using a column containing SEPHADEX™ G50 Fine in the above buffer with 0.1 mM EDTA present.

The AP and the derivatized antibody were mixed together in a molar ratio of 1:1 and the conjugation reaction was allowed to continue overnight at room temperature. To stop the conjugation, 2-mercaptoethanol was added to 1 mM final concentration to the conjugate solution and reacted for 5 minutes followed by the addition of N-ethyl maleimide to 2 mM final concentration. The conjugate was purified by gel filtration chromatography using Sephacryl S-500 HR (Pharmacia Biotech, Piscataway, N.J.). The free antibody was excluded from the conjugate pool which was diluted for use in immunoassays using the conjugate diluent described above.

C. Preparation of Capture Moiety

The monoclonal antibody 7F11, which specifically binds to the decapeptide sequence YPYDVPDYAS (SEQ ID NO. 5), was prepared as described above. To construct the capture moiety, the antibody 7F11 was coupled to magnetic particles as follows. Amine terminated BioMag™ particles (PerSeptive Biosystems, Framingham, Mass.) with a nominal size distribution of 2.5 μm were initially washed with deionized water. A volume of 52.6 ml of 3.8% particles was washed by magnetic separation from the storage solution followed by resuspension in deionized water and magnetic separation using permanent magnets obtained from PerSeptive Biosystems. The BioMag particles were resuspended in 188 ml of deionized water and 20 ml of 500 mM potassium phosphate, 100 mM borate, pH 7.0, was added and mixed. The crosslinking agent SMCC (124 mg) was dissolved in 20 ml of dry N,N-dimethylformamide (DMF, Aldrich Chemical Co., Milwaukee, Wis.) and the solution was added to the BioMag suspension. The reaction was allowed to proceed with gentle rocking for two hours at room temperature. To stop the reaction, 2-aminoethanesulfonic acid was added to a final concentration of 20 mM and reacted for 15 minutes at room temperature. The BioMag was washed five times using magnetic separation with five 200-ml volumes of 50 mM potassium phosphate, 10 mM borate, 10% DMF, pH 7.0. The SMCC-BioMag particles were resuspended in 100 ml of 50 mM potassium phosphate, 10 mM borate, 150 mM sodium chloride, 0.1 mM EDTA, pH 7.0.

The monoclonal antibody 7F11 was derivatized by diluting to 5 mg/ml and mixing 100 ml of this solution with 5.2 mg of SPDP that had been dissolved in 0.2 ml of acetonitrile. The reaction was allowed to proceed for 90 minutes at room temperature before 2-aminoethanesulfonic acid was added to a final concentration of 20 mM and reacted for 15 minutes. DTT was added to a final concentration of 2 mM and reacted for 30 minutes at room temperature. The antibody solution was concentrated to 20 ml using a YM 30 ultrafiltration membrane (Amicon, Beverly, Mass.) and the antibody was subjected to gel filtration chromatography using a column containing SEPHADEX ™ GH-25 (Amicon, Beverly, Mass.) in 50 mM potassium phosphate, 10 mM borate, 150 mM sodium chloride, 0.1 mM EDTA, pH 7.0. The antibody eluting from the column was collected and diluted to 100 ml with the same buffer.

The SPDP-derivatized antibody 7F11 was then mixed with the SMCC-BioMag particle suspension. The final antibody concentration was 2.3 mg/ml and the final particle concentration was 1% solids. The reaction proceeded for 18 hours at room temperature with gentle rocking before it was stopped by adding 2-mercaptoethanol to a final concentration of 2 mM followed by a 30-minute incubation and the addition of N-hydroxyethylmaleimide to a final concentration of 6 mM. The 7F11-BioMag was washed five times with five 200-ml volumes of 50 mM potassium phosphate, 10 mM borate, 150 mM sodium chloride, pH 7.0, using magnetic separation and the particles were stored at 1% solids in this buffer containing 0.1% sodium azide.

D. Preparation of Toxin A Binding Moiety

The toxin A binding moiety was based on the monoclonal antibody PCG-4, which specifically binds to *C. difficile* toxin A and is described in U.S. Pat. No. 4,533,630. A barbiturate derivative was attached to the antibody as a hapten to bind the detection moiety, and a decapeptide sequence was attached to the antibody as a molecular tag to bind the capture moiety.

To attach the barbiturate derivative to monoclonal antibody PCG-4, the antibody was prepared at 10 mg/ml in 50 mM potassium phosphate, 10 mM borate, 150 mM sodium chloride, 0.1 mM EDTA, pH 7.0. SMCC was added to a final molar ratio of 25:1 SMCC:antibody using a solution of SMCC at 20 mg/ml in acetonitrile. The reaction was allowed to proceed for 90 minutes at room temperature prior to separation of the antibody from the SMCC by gel filtration chromatography in a column containing G50 Fine in the above buffer. The SMCC-PCG-4 was collected and the concentration determined by $A_{280}$ using an absorbance of 1.4 for a 1 mg/ml solution.

Barbiturate derivative was dissolved in 70% DMF and 1 N potassium hydroxide was added to a final concentration of 0.2 N while mixing vigorously. The derivative solution was allowed to stand for 5 minutes at room temperature prior to neutralization of the solution by the addition of a solution containing 0.5 M potassium phosphate, 0.1 M borate, pH 7.0, to which concentrated hydrochloric acid has been added to a concentration of 1 M. The thiol concentration of the hydrolyzed barbiturate derivative was determined by diluting 2 μL of the solution into 998 μL of a solution containing 0.25 mM 5,5'-dithiobis(2-nitrobenzoic acid) (DTNB, Aldrich Chemical Co., Milwaukee Wis.) and 0.2 M potassium borate, pH 8.0. The thiol concentration in mM units was equal to the $A_{412}(500/13.76)$.

The decapeptide derivative was similarly prepared by hydrolysis and its thiol concentration was also determined.

The barbiturate and decapeptide derivatives were attached to the derivatized PCG-4 antibody as follows. The SMCC-PCG-4 preparation was typically at a concentration of 2–3 mg/ml. The hydrolyzed barbiturate and decapeptide derivatives were mixed together so that when added to the antibody solution, the final thiol concentration was 0.3 mM and the ratio of hydrolyzed barbiturate derivative to hydrolyzed decapeptide derivative was 2:1. The reaction was allowed to proceed for 30 minutes at room temperature before the barbiturate/decapeptide-PCG-4 antibody was placed into dialysis vs. one liter of BBS.

E. High Sensitivity Assay for Toxin A

The assay was carried out essentially as shown in FIG. 2. Barbiturate/decapeptide-PCG-4 antibody (toxin A binding moiety) was added to 7F11-BioMag (capture moiety) to a final concentration of approximately 50 μg/ml of 7F11-BioMag at 1% solids. The antibody was allowed to bind via the affinity of 7F11 for the decapeptide derivative for 5 minutes prior to washing the BioMag with one volume of dissociation buffer followed by one volume of neutralization buffer followed by three volumes of 50 mM potassium phosphate, 10 mM borate, 150 mM sodium chloride, pH 7.0, with final storage at 1% solids in this buffer.

Stool samples were taken in amounts of 5 grams or 5 ml and diluted to 40 ml with a sample diluent containing 10 mM potassium phosphate, 150 mM sodium chloride, 0.1% casein, 0.01% bovine IgG, 0.05% t-octylphenoxypolyethoxyethanol (TRITON X-100™), pH 7.6. The diluted samples were filtered through glass wool to remove large debris and 400 μL of barbiturate/decapeptide-PCG-4-7F11-Biomag was added to the diluted sample in a 50-ml conical tube. The mixture was placed on a rocker to keep the BioMag suspended for 30–60 minutes at room temperature. The samples were then placed on a magnetic separation rack (Perseptive Biosystems, Framingham, Mass.) and the BioMag was allowed to separate from the sample for 5 minutes. The liquid was decanted from the sample container and discarded, the BioMag was resuspended in the sample diluent, and the sample container was placed back in the magnetic separation rack for another five minutes. The solution was decanted again and discarded.

To dissociate the binding of the capture moiety to the decapeptide sequence, the BioMag complex was resuspended in 300 μL of dissociation buffer containing 50 mM potassium phosphate, 150 mM NaCl, pH 11.5. The BioMag was incubated for two minutes in this solution before separation of the BioMag from the solution in the magnetic separation rack. The solution was removed and subjected to centrifugation for approximately 20,000 g min. The clarified solution was removed from the centrifuge tube and neutralized by adding 200 μL of a neutralization buffer containing 200 mM N-[2-hydroxyethyl]piperazine-N'-[3-propanesulfonic acid] (HEPPS, Calbiochem, LaJolla Calif.), 150 mM sodium chloride, 0.8% casein, 0.15 sodium azide, 50 μM decapeptide derivative that had been hydrolyzed and reacted with N-ethylmaleimide, pH 7.3.

The sample was then added to an immunoassay device as described above containing a line of immobilized polyclonal antibody specific for toxin A, CD.TXA.1.PC, conjugated to casein. Preparation of this antibody, which is a recombinant polyclonal antibody, is described in co-filed U.S. patent application Ser. No. 08/832,985 (filed Apr. 4, 1997. The antibody was immobilized on the porous membrane of the assay device as described above, using a solution containing approximately 5 mg/ml of antibody. After the sample drained into the device, the conjugate of 3E12 and alkaline phosphatase was added in a volume of 140 $\mu$L at a concentration of approximately 20 $\mu$g/ml in the conjugate diluent described above and allowed to react for 3 minutes at room temperature.

After the incubation, five drops of wash solution containing 100 mM tris (hydroxymethyl) aminomethane (TRIS, Fisher Scientific, Pittsburgh, Pa.), 150 mM sodium chloride, 0.5% Dow 193 surfactant, 0.1% sodium azide, and 20 mg/L of NBT were applied from a dropper bottle. After the wash drained into the membrane, another five drops of wash solution were applied and allowed to drain. Three drops of substrate solution containing 10 mM indoxyl phosphate (JBL Scientific, San Luis Obispo, Calif.), 200 mM 2-amino-2-methyl-1-propanol (JBL Scientific, San Luis Obispo, Calif.), 500 mM TRIS, pH 10.2, were added from a dropper bottle and the device was incubated for five minutes at room temperature. At the end of the incubation time the presence of a visually detectable purple to black line at the detection zone for toxin A was noted as a positive result. The absence of a visually detectable line at this zone was a negative result.

The sensitivity of this assay was measured by spiking toxin A into 5 ml volumes of sample diluent at 0.1, 0.05, 0.02, 0.01, and 0 ng/ml and performing the assay as described. The devices containing toxin A at 0.01 ng/ml and above exhibited faint but visible purple to black lines at the detection zone for toxin A. No visible line was present at the detection zone for toxin A in the device used to test the sample containing 0 ng/ml toxin A. Six patient samples were identified which had yielded positive results for the glutamate dehydrogenase assay described in Example I-D but were negative in the toxin A assay described above and had originally been determined to be negative by the toxin assay method employed at the laboratory that supplied the sample. These six samples were tested using the high sensitivity assay for toxin A and two of the samples resulted in clearly visible lines at the toxin A detection zone indicating positive results for the presence of toxin A. These results show the value of the glutamate dehydrogenase assay in identifying samples that contain toxigenic organisms that are being classified as falsely negative by the conventional methods II. High Sensitivity Assay for Toxigenic *C. difficile* Strains in Stool Samples by Amplification of Genes Encoding Toxin A, Toxin B, and Glutamate Dehydrogenase The procedure is an extension of the method described by Lou et. al., *J. Clin. Microbiol.* (January 1997) 35: 281–283. Approximately 200 mg of stool was diluted to 500 µL with sterile water in a 1.5-ml polypropylene microcentrifuge tube. The sample was boiled in a water bath for 5 minutes to lyse bacteria, after which the sample was clarified by centrifugation at 14,000 rpm for 5 minutes in a high speed microcentrifuge. Approximately 250 µL of the supernatant was transferred to a new tube. A mixture of 10 µL of the clarified sample, 30 µL of sterile water, and 10 µL of loading buffer containing 25% glycerol, 2% sodium dodecyl sulfate (SDS), 0.05% bromophenol blue, and 0.05% xylene cyanol was incubated at 70° C. in a water bath for 15 minutes. This solution was loaded onto a spin column containing an agarose-base gel filtration medium such as SEPHAROSE™ CL-6B (Pharmacia, Piscataway, N.J.) and subjected to centrifugation for 3 minutes at 2000 rpm (330g).

The resulting eluant from the column was used for PCR. Three sets of primers were used to amplify fragments of the genes for toxin B, toxin A, and glutamate dehydrogenase. The primers used to amplify a 399-bp fragment of toxin B were the same as described in Lou et al. A 430-bp fragment of toxin A was amplified using the primers #649 (SEQ ID NO: 6; ATGTAGAAGTAAACTTACTTGGATG) and #650 (SEQ ID NO: 7; CCCCAATAGAAGATTCAATATTAAG). A 690-bp fragment of the glutamate dehydrogenase gene was amplified using the primers #659 (SEQ ID NO: 8; AAGTGTTCTGTAACAGGTATACC) and #660 (SEQ ID NO: 9; GGTCCATTAGCAGCCTCACA).

Amplifications were performed in 50 µL reactions using 10 µL of template DNA and the Expand High Fidelity PCR System (Boehringer Mannheim, Indianapolis Ind.), 5 µL Expand 10×HF buffer+MgCl$_2$ to 2 mM, 5 µL of 2 mM dNTPs, 0.05 µM of each PCR primer, and 1.25 U of Expand HF polymerase. After a 10-minute denaturation at 94° C., the PCR mixtures were subjected to 15 cycles of amplification at 94° C. (30 s), 55° C. (30 s), and 72° C. (45 s) followed by 20 cycles of amplification at 94° C. (30 s), 55° C. (30 s), and 72° C. (65 s+20 s each additional cycle) and a 6-minute hold/extension at 72° C. The PCR products were electrophoresed on either 1.5% agarose or 6% polyacrylamide and stained with either ethidium bromide or SYBR green (Molecular Probes, Eugene, Oreg.) to determine the size of the fragments.

A total of seventeen stool samples were prepared and subjected to PCR for the fragments of the toxin A gene, the toxin B gene, and the glutamate dehydrogenase gene described above. The seventeen stool samples were each positive in the immunoassay for glutamate dehydrogenase with a sensitivity of 2 ng/ml and negative in the immunoassay for toxin A with a sensitivity of 2 ng/ml. Fifteen of the samples were originally reported to be negative by the hospital or reference laboratory using either a toxin A immunoassay or cytotoxin assay and two of the samples were reported to be positive. Fourteen of the fifteen samples originally reported as negative exhibited gene fragments of the expected size following PCR using the designated primers for toxin A, toxin B, and glutamate dehydrogenase. Samples containing non-toxigenic strains of *C. difficile* were also tested and resulted in no amplified fragments for either the toxin A or the toxin B genes but did exhibit an amplified fragment of the glutamate dehydrogenase gene. Two samples originally reported positive by the hospital or reference laboratory were negative for toxin A and positive for glutamate dehydrogenase using the immunoassays with sensitivities of 2 ng/ml. These samples were negative by PCR for toxin A and toxin B but positive for glutamate dehydrogenase. Thus, fourteen of seventeen samples randomly selected but positive for glutamate dehydrogenase and negative for toxin A by immunoassay were found to be toxigenic in that they harbor the genes for toxin A and toxin B.

Hybridomas or cells producing antibodies CD.TXA.1.PC (ATCC 98388, Apr. 3, 1997), CD.43.9 (ATCC 98390, Apr. 3, 1997), CD.43.5.PC (ATCC 98389, Apr. 3, 1997), 3E12 (ATCC HB-12442, Dec. 5, 1997), and 7F11 (ATCC HB-12443, Dec. 5, 1997) were deposited with the American Type Culture Collection, 10801 University Boulevard, Manassas, Va. 20110-2209, under the Budapest Treaty on the dates indicated and given the Accession Nos. indicated. These cell lines will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for detecting the presence of a toxigenic strain of *C. difficile* in a test sample, the method comprising the steps of:
   a) testing for the presence of *C. difficile* glutamate dehydrogenase in the test sample using an assay that can detect 100 ng or less glutamate dehydrogenase per ml of sample; and
   b) if *C. difficile* glutamate dehydrogenase is present in the test sample, testing for the presence of *C. difficile* toxin A or toxin B, or a nucleic acid encoding *C. difficile* toxin A or toxin B or a portion thereof, in the test sample, wherein a positive result of the testing indicates the presence of a toxigenic strain of *C. difficile* in the test sample.

2. The method according to claim 1, wherein the testing for the presence of *C. difficile* toxin A or toxin B comprises using an assay that has a sensitivity of at least 2 ng toxin per ml.

3. The method according to claim 1, wherein the testing for the presence of a nucleic acid encoding toxin A or toxin B comprises amplification of the nucleic acid, or a portion thereof, and detecting the presence of the amplified nucleic acid.

4. The method according to claim 3, wherein the amplification is achieved using polymerase chain reaction.

5. The method according to claim 3, wherein the method further comprises amplification of a nucleic acid that encodes *C. difficile* glutamate dehydrogenase, or a portion thereof.

6. The method according to claim 3, wherein the method comprises testing for the presence of a nucleic acid that encodes *C. difficile* toxin A and a nucleic acid that encodes *C. difficile* toxin B, or portions of each thereof.

7. The method according to claim 1, wherein the testing for the presence of *C. difficile* toxin B comprises performing a cytotoxicity assay.

8. The method according to claim 1, wherein the assay used to test for the presence of *C. difficile* glutamate dehydrogenase is an immunoassay.

9. The method according to claim 1, wherein the testing for the presence of *C. difficile* toxin B comprises:
   contacting the test sample with an anchor moiety that is immobilized on a solid support and can specifically bind to at least a first epitope of *C. difficile* toxin B;
   contacting the bound *C. difficile* toxin B with one or more detection moieties, each of which is conjugated to a detectable label and can specifically bind to at least a second epitope of *C. difficile* toxin B; and detecting the presence of the detectable label bound to *C. difficile* toxin B, wherein the presence of the detectable label bound to *C. difficile* toxin B indicates the presence of *C. difficile* toxin B.

10. The method according to claim 1, wherein the testing for the presence of *C. difficile* toxin B comprises:

adding to the test sample a toxin B binding moiety that specifically binds to *C. difficile* toxin B to form a toxin B binding moiety-toxin B complex;

adding to the test sample a magnetic bead to which is attached a capture moiety that specifically binds to the toxin B binding moiety to form a magnetic bead-binding moiety-toxin B complex;

separating the magnetic bead-binding moiety-toxin B complex from the test sample;

dissociating the toxin B binding moiety-toxin B complex from the magnetic bead and removing the magnetic bead from the solution containing the binding moiety-toxin B complex; and detecting the presence of the toxin B binding moiety-toxin B complex, wherein the presence of the toxin B binding moiety-toxin B complex indicates the presence of *C. difficile* toxin B in the test sample.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Asp Tyr Lys Asp Asp Asp Asp Lys
1               5

(2) INFORMATION FOR SEQ ID NO:2:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

GACTACAAGG ACGACGATGA CAAG                                              24

(2) INFORMATION FOR SEQ ID NO:3:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:3:

Asp Tyr Lys Asp
1

(2) INFORMATION FOR SEQ ID NO:4:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Asp Tyr Lys Asp Glu
1               5

(2) INFORMATION FOR SEQ ID NO:5:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Tyr Pro Tyr Asp Val Pro Asp Tyr Ala Ser
1               5                   10

(2) INFORMATION FOR SEQ ID NO:6:

(i) SEQUENCE CHARACTERISTICS:
            (A) LENGTH: 25 base pairs
            (B) TYPE: nucleic acid
            (C) STRANDEDNESS: single
            (D) TOPOLOGY: linear

```
        (ii) MOLECULE TYPE: DNA (xi) SEQUENCE DESCRIPTION: SEQ ID NO:6:

ATGTAGAAGT AAACTTACTT GGATG                                             25

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

CCCCAATAGA AGATTCAATA TTAAG                                             25

(2) INFORMATION FOR SEQ ID NO:8:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

AAGTGTTCTG TAACAGGTAT ACC                                               23

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

GGTCCATTAG CAGCCTCACA                                                   20
```